United States Patent
Madsen et al.

[11] Patent Number: 6,090,797
[45] Date of Patent: Jul. 18, 2000

[54] 4,5,6,7-TETRAHYDRO-THIENO(2,3-C) PYRIDINE DERIVATIVES

[75] Inventors: Peter Madsen, Bagsvaerd; Jane Marie Lundbeck, Glostrup; Niels Westergaard; Palle Jakobsen, both of Vaerlose, all of Denmark

[73] Assignee: Novo Nordisk A/S, Bagsvaerd, Denmark

[21] Appl. No.: 09/387,290

[22] Filed: Aug. 31, 1999

Related U.S. Application Data

[60] Provisional application No. 60/099,930, Sep. 11, 1998.

[30] Foreign Application Priority Data

Sep. 2, 1998 [DK] Denmark ............................ 1998 01108

[51] Int. Cl.[7] ..................... A61K 31/435; C07D 471/04
[52] U.S. Cl. ........................... 514/114; 544/362; 546/114
[58] Field of Search .............................. 546/114; 514/301

[56] References Cited

U.S. PATENT DOCUMENTS

| | | | |
|---|---|---|---|
| 3,334,086 | 8/1967 | Ott | 546/114 |
| 3,497,529 | 2/1970 | Ott | 260/332.2 |
| 4,075,340 | 2/1978 | Maffrand et al. | 546/114 |
| 4,076,819 | 2/1978 | Maffrand et al. | 546/114 |
| 5,294,621 | 3/1994 | Russell | 546/114 |

FOREIGN PATENT DOCUMENTS

| | | |
|---|---|---|
| WO 92/15592 | 9/1992 | WIPO . |
| WO 96/34870 | 11/1996 | WIPO . |
| WO 98/40385 | 9/1998 | WIPO . |

OTHER PUBLICATIONS

CA 112:158190, 1990.
CA 111:39219, 1989.
CA 85:160017, 1976.
CA 79:49080, 1973.
CA 72:100743, 1970.
Gray et al, J. Med. Chem., 32, pp. 1242–1248, 1989.
Dressler et al, J. Het. Chem., 7(6), pp. 1257–1268, 1970.
Chem Abstract No. 99:175627 (1983).
Chem Abstract No 111:39219 (1989).
Chem Abstract No. 79:49080 (1973).
Chem Abstract No. 114:122254 (1991).
Chem Abstract No. 85:160017 (1976).

*Primary Examiner*—Bernard Dentz
*Attorney, Agent, or Firm*—Steve T. Zelson; Carol E. Rozek

[57] ABSTRACT

Disclosed are compounds of formula (I)

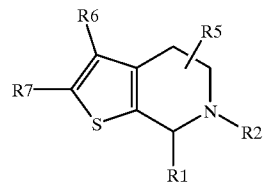

Formula (I)

wherein
R1 is $C_{1-8}$-alkyl, $C_{2-8}$-alkenyl, $C_{3-8}$-cycloalkyl, $C_{5-8}$-cycloalkenyl, Q or aryl;
R2 is $C_{1-8}$-alkyl, $C_{2-8}$-alkenyl, $C_{3-8}$-cycloalkyl, $C_{5-8}$-cycloalkenyl, aralkyl or COR3;
R3 is $C_{1-8}$-alkyl, $C_{2-8}$-alkenyl, $C_{3-8}$-cycloalkyl, $C_{5-8}$-cycloalkenyl, w or aryl;
R5, R6 and R7 are independently selected from amino-$C_{1-6}$-alkyl, hydroxy-$C_{1-6}$-alkyl, hydrogen, $C_{1-6}$-alkyl, aryl, aralkyl, aryloxy, aryloxy-$C_{1-6}$-alkyl, benzyl, halogen, hydroxy, mercapto, cyano, nitro, carboxy, carbamoyl, $CONHC_{1-4}$-alkyl, $CON(C_{1-4}alkyl)_2$, $C_{1-4}$-acyl, $C_{1-4}$-alkoxy, $C_{1-4}$-alkylthio, —$SOC_{1-6}$-alkyl, —$SO_2C_{1-6}$-alkyl, $C_{1-4}$-alkoxycarbonyl, $C_{1-4}$-alkanoyloxy, amino, optionally substituted mono- or di-$C_{1-6}$-alkylamino, acylamino, —$NC_{1-4}$-alkyl$COC_{1-4}$-alkyl, —$SO3H$, —$SO2NH$—$C_{1-6}$-alkyl, tetrazolyl, perhalomethyl, perhalomethoxy;
wherein R1, R2 and R3 are all optionally substituted with one or more substituents;
or salt thereof with a pharmaceutically acceptable acid or base, or any optical isomer; a pharmaceutical composition containing them, and the use of these compounds for preparing medicaments for the treatment of diseases of the endocrinologic system, preferably hyperglycemia or diabetes.

26 Claims, No Drawings

4,5,6,7-TETRAHYDRO-THIENO(2,3-C) PYRIDINE DERIVATIVES

CROSS-REFERENCE TO RELATED APPLICATIONS

This application claims priority under 35 U.S.C. 119 of U.S. provisional application Ser. No. 60/099,930 filed Sep. 11, 1998 and Danish application no. PA 1998 01108 filed Sep. 2, 1998, the contents of which are fully incorporated herein by reference.

FIELD OF THE INVENTION

The present invention relates to 4,5,6,7-tetrahydro-thieno [2,3-c]pyridine derivatives, to compositions comprising the compounds, to the use of these compounds as medicaments and their use in therapy, e.g. to their use for treatment of human and animal disorders. The invention relates to modulation of the activity of molecules with glucose-6-phosphate recognition units, including glucose-6-phosphatases (G-6-Pases) in in vitro systems, microorganisms, eukaryotic cells, whole animals and human beings, especially in the treatment of diseases related to glucose metabolic pathways.

BACKGROUND OF THE INVENTION

Glucose is the major energy substrate in mammals and regulation of blood glucose levels within a narrow range seems to be of crucial importance to devoid serious physiological complications as seen in diabetes (DeFronzo, Bonadonna, & Ferrannini. 1992). Blood glucose homeostasis is maintained by dietary intake of carbohydrates, the uptake of glucose by peripheral tissues and the brain, and storage or release of glucose from the liver. The liver therefore seems to play a major role in the homeostatic regulation of blood glucose levels. Gluconeogenesis and glycogenolysis are the two metabolic pathways from which glucose can be produced in the liver. These pathways are under tight hormonal control. Insulin resistance and insulin deficiency have a substantial impact on glucose production in the liver (Consoli. 1992; DeFronzo, Bonadonna, & Ferrannini. 1992; Clore, Stillman, Stevens, Blackard, Levy, & Richmond. 1996). Glucose-6-phosphatase (G-6-Pase) catalyzes the terminal step in the above mentioned pathways by converting glucose-6-phosphate (G-6-P) to glucose, and is largely situated in the liver, with some expression in the kidney after prolonged fasting. The G-6-Pase is a multicomponent system comprising of the G-6-Pase catalytic enzyme with its active site located at the luminal site of the endoplasmic reticulum (microsomal fraction), a specific transporter T1 which mediates entry of G-6-P into the luminal compartment, and transporter T2 and T3 which mediates export to the cytosol of inorganic phosphate and glucose, respectively (Nordlie, Bode, & Foster. 1993; Sukalski & Nordlie. 1989). It has been shown that the rate of hydrolysis of G-6-P and the hepatic glucose output were increased under diabetic conditions (Lyall, Grant, Scott, & Burchell. 1992; DeFronzo, Bonadonna, & Ferrannini. 1992). The increased activity could mainly be accounted for by increased G-6-Pase catalytic enzyme protein (Argaud, Zhang, Pan, Maitra, Pilkis, & Lange. 1996; Burchell & Cain. 1985). This makes G-6-Pase enzyme a potential target in control of excess glucose production seen in diabetes.

BIBLIOGRAPHY

Argaud, D., Zhang, Q., Pan, W., Maitra, S., Pilkis, S. J., & Lange, A. (1996). Regulation of rat liver glucose-6-phosphatase gene expression in different nutritional and hormonal states. *Diabetes*, 45:1563–1571.

Arion, J. M., Lange, A. J., & Walls, H. E. (1980). Microsomal membrane integrity and the interactions of phlorizin with the glucose-6-phosphatase system. *J Biol Chem*, 255:10387–10395.

Burchell, A., & Cain, D. I. (1985). Rat hepatic microsomal glucose-6-phosphatase protein levels are increased in streptozotocin-induced diabetes. *Diabetologia*, 28: (852). 856

Clore, J. N., Stillman, J. S., Stevens, W., Blackard, W. G., Levy, J., & Richmond, V. A. (1996). Chronic hyperinsulinemia supresses glucose-6-phosphatase mRNA. *Diabetes*, 44 (suppl 1):253A Consoli, A. (1992). Role of liver in pathophysiology of NIDDM. *Diabetes Care*, 15:430–441.

DeFronzo, R. A., Bonadonna, R. C., & Ferrannini, E. (1992). Pathogenesis of NIDDM: A Balanced overview. *Diabetes Care*, 15:318–368.

Lyall, H., Grant, A., Scott, H. M., & Burchell, A. (1992). Regulation of the hepatic microsomal glucose-6-phosphatase enzyme. *Biochem Soc Trans*, 20, 271S (abstract).

Nordlie, R. C., Bode, A. M., & Foster, J. D. (1993). Recent advances in hepatic glucose 6-phosphatase regulation and function. *Proc Soc Exp Biol Med*, 203:274–285.

Sukalski, K. A., & Nordlie, R. C. (1989). Glucose-6-phosphatase: Two concepts of membrane function relationship. In A. Meister (Ed.), *Advances in Enzymology and realted areas of molecular biology.* (pp. 93–117). New York: John Wiley and Sons.

DESCRIPTION OF THE INVENTION

The present invention relates to compounds of formula (I):

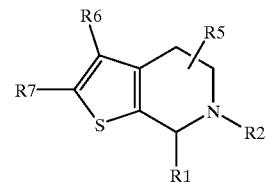

Formula (I)

wherein

R1 is a saturated straight or branched $C_{1-8}$-hydrocarbon chain optionally substituted with one or more substituents, an unsaturated straight or branched $C_{2-8}$-hydrocarbon chain optionally substituted with one or more substituents, a saturated $C_{3-8}$-alicyclic hydrocarbon group optionally substituted with one or more substituents, an unsaturated $C_{5-8}$-alicyclic hydrocarbon group optionally substituted with one or more substituents, Q optionally substituted with one or more substituents or aryl optionally substituted with one or more substituents;

R2 is a saturated straight or branched $C_{1-8}$-hydrocarbon chain optionally substituted with one or more substituents, an unsaturated straight or branched $C_{2-8}$-hydrocarbon chain optionally substituted with one or more substituents, a saturated $C_{3-8}$-alicyclic hydrocarbon group optionally substituted with one or more substituents, an unsaturated $C_{5-8}$-alicyclic hydrocarbon group optionally substituted with one or more substituents, aralkyl optionally substituted with one or more substituents or COR3 optionally substituted with one or more substituents;

R3 is a saturated straight or branched $C_{1-8}$-hydrocarbon chain optionally substituted with one or more substituents, an unsaturated straight or branched $C_{2-8}$-hydrocarbon chain optionally substituted with one or more substituents, a saturated $C_{3-8}$-alicyclic hydrocarbon group optionally substituted with one or more substituents, an unsaturated $C_{5-8}$-alicyclic hydrocarbon group optionally substituted with one or more substituents, an aryl optionally substituted with one or more substituents, an aralkyl optionally substituted with one or more substituents or W optionally substituted with one or more substituents;

Q and W are independently selected from the list consisting of

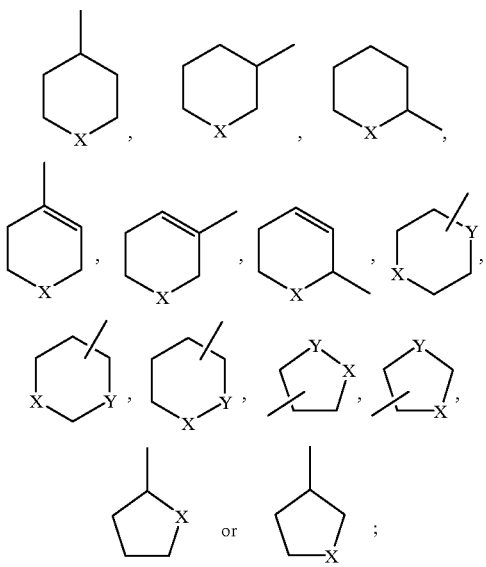

X and Y are independently selected from the group consisting of NR4, O, S, >SO, >SO$_2$;

and R4 is selected from the list consisting of hydrogen, a saturated straight or branched $C_{1-8}$-hydrocarbon chain optionally substituted with one or more substituents, an unsaturated straight or branched $C_{2-8}$-hydrocarbon chain optionally substituted with one or more substituents, a saturated $C_{3-8}$-alicyclic hydrocarbon group optionally substituted with one or more substituents, an unsaturated $C_{5-8}$-alicyclic hydrocarbon group optionally substituted with one or more substituents, $C_{1-8}$-acyl, $C_{1-8}$-alkoxycarbonyl, or mono- or dialkylcarbamoyl;

R5, R6, R7 are independently selected from amino-$C_{1-6}$-alkyl, hydroxy-$C_{1-6}$alkyl, hydrogen, $C_{1-6}$-alkyl, aryl, aralkyl, aryloxy, aryloxy-$C_{1-6}$-alkyl, benzyl, halogen, hydroxy, mercapto, cyano, nitro, carboxy, carbamoyl, CONHC$_{1-4}$-alkyl, CON(C$_{1-4}$alkyl)$_2$, $C_{1-4}$-acyl, $C_{1-4}$-alkoxy, $C_{1-4}$-alkylthio, —SOC$_{1-6}$-alkyl, —SO$_2$C$_{1-6}$-alkyl, $C_{1-4}$-alkoxycarbonyl, $C_{1-4}$-alkanoyloxy, amino, optionally substituted mono- or di-$C_{1-6}$-alkylamino, acylamino, —NC$_{1-4}$-alkylCOC$_{1-4}$-alkyl, —SO$_3$H, —SO$_2$NH—C$_{1-6}$-alkyl, tetrazolyl, perhalomethyl, perhalomethoxy each of the above substituents being selected from the group consisting of halogen, hydroxyl, carboxy, carboxyalkenyl, 2-carboxyethenyl, cyano, nitro, carbamoyl, $C_{1-8}$-alkylcarbamoyl (preferably metanoyl), $C_{1-8}$-acyl (preferably acetyl, propionyl, isopropionyl), acetamido, $C_{1-8}$-alkoxy (preferably methoxy, ethoxy, propoxy, isopropoxy, butoxy, and tert.butoxy), $C_{1-8}$-alkyl, $C_{1-8}$-alkoxycarbonyl (preferably methoxycarbonyl, ethoxycarbonyl, and propoxycarbonyl), $C_{1-8}$-alkanoyloxy (preferably acetyloxy, propionyloxy, isopropionyloxy), $C_{1-4}$-alkylthio (preferably methylthio, ethylthio, propylthio, and isopropylthio), $C_{1-4}$-alkylsulphinyl (preferably methylsulphinyl and ethylsulphinyl), $C_{1-4}$-alkylsulphonyl (preferably methylsulphonyl and ethylsulphonyl), $C_{1-8}$-alkylamino (preferably methylamino, ethylamino), $C_{1-8}$-dialkylamino (preferably dimethylamino, diethylamino) $C_{2-6}$-cycloamines (preferably 1-piperidinyl, 1-azeridinyl, 1-pyrrolidinyl, 4-morpholinyl, 1-piperazinyl, 1-azetidinyl), aminoalkyl (preferably one having an amino containing group connected to a $C_{1-8}$-alkyl group as defined above, such as 2-dimethylaminoethyl and 1-pyrrolidinylmethyl), aminoalkoxy (preferably one having an amino containing group connected via a $C_{1-8}$-alkyl group as defined above to an oxygen atom, such as 2-dimethylaminoethoxy, 2-(4-morpholinyl)ethoxy and 1-pyrrolidinylmethoxy), aryl (preferably phenyl, furanyl and 4-pyridinyl), aryloxy (preferably phenyloxy), and aralkyloxy (e.g. benzyloxy), hydroxyalkyl, perhaloalkoxy (preferably trifluromethoxy), alkoxyaryl, $C_{1-8}$-acyl, perhaloalkyl (preferably trifluoromethyl), oxo, $C_{1-4}$-alkanoylamino-$C_{1-4}$-alkyl, alkoxyoxoindanyl, dimethylhydrazidyl, methylendioxy, thioxothiazolyl, imidazolyl or 2-morpholin-4-ylethoxy;

or a salt thereof with a pharmaceutically acceptable acid or base, or any optical isomer or mixture of optical isomers, including a racemic mixture, or any tautomeric form.

In a preferred embodiment the invention relates to compounds of formula (I) wherein R5, R6 and R7 are hydrogen.

In another preferred embodiment the invention relates to compounds of formula (I), wherein R2 is COR3 and R3 is as defined above.

In another preferred embodiment the invention relates to compounds of formula (I), wherein R1 is Q optionally substituted with one or more substituents and Q is

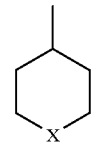

wherein X is as defined above.

In another preferred embodiment the invention relates to compounds of formula (I), wherein X is NR4 or O, preferably NR4, wherein R4 is as defined above.

In another preferred embodiment the invention relates to compounds of formula (I), wherein R4 is a saturated straight or branched $C_{1-8}$-hydrocarbon chain optionally substituted with one or more substituents.

In another preferred embodiment the invention relates to compounds of formula (I), wherein R4 is methyl.

In another preferred embodiment the invention relates to compounds of formula (I), wherein R1 is Q optionally substituted with one or more substituents and Q is

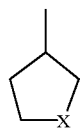

wherein X is as defined above.

In another preferred embodiment the invention relates to compounds of formula (I), wherein X is O.

In another preferred embodiment the invention relates to compounds of formula (I), wherein R1 is N-methylpiperidinyl, tetrahydrofuryl or tetrahydropyranyl.

In another preferred embodiment the invention relates to compounds of formula (I), wherein R1 is tetrahydropyran-4-yl, tetrahydrofuran-3-yl or 1-methylpiperidin-4-yl.

In another preferred embodiment the invention relates to compounds of formula (I), wherein R1 is optionally substituted phenyl, thienyl, preferably 2-thienyl, 3-thienyl, 4-thienyl or 5-thienyl, or furanyl, preferably 2-furanyl, 3-furanyl, 4-furanyl, or 5-furanyl, Benzo[1,3]dioxol, preferably Benzo[1,3]dioxol-5yl, pyridyl or cyclohexyl.

In another preferred embodiment the invention relates to compounds of formula (I), wherein the substituents of R1 are selected from the group consisting of halogen, perhaloalkyl, perhaloalkoxy, $C_{1-6}$-alkoxy, $C_{1-8}$-alkyl, $C_{1-8}$-alkylamino, $C_{1-8}$-dialkylamino and $C_{2-5}$-cycloalkylamino.

In another preferred embodiment the invention relates to compounds of general formula (I), wherein the substituents of R1 are selected from the group consisting of chloro, fluoro trifluoromethyl, trifluoromethoxy, methoxy, methyl and dimethylamino.

In another preferred embodiment the invention relates to compounds of formula (I), wherein R1 is selected from the group consisting of phenyl, 4-chlorophenyl, 3-fluorophenyl, 2,4-chlorophenyl, 3,5-chlorophenyl, 2-methoxyphenyl, 3-methoxyphenyl, 4-methoxyphenyl, 2,4-methoxyphenyl, 3-fluoro-4-methoxyphenyl, 4-trifluoromethylphenyl, 4-trifluoromethoxyphenyl, 4-dimethylaminophenyl, 4-pyridyl, 2-thienyl, 5-chloro-2-thienyl, 3-chloro-2-thienyl, Benzo[1,3]dioxol-5yl, cyclohexyl and 4-methoxycyclohexyl.

In another preferred embodiment the invention relates to compounds of formula (I), wherein R3 is a saturated straight or branched $C_{1-8}$-hydrocarbon chain optionally substituted with one or more substituents.

In another preferred embodiment the invention relates to compounds of formula (I), wherein R3 is a saturated straight or branched $C_{1-3}$-alkyl optionally substituted with one or more substituents.

In another preferred embodiment the invention relates to compounds of formula (I), wherein R3 is an unsaturated straight or branched $C_{2-8}$-hydrocarbon chain optionally substituted with one or more substituents.

In another preferred embodiment the invention relates to compounds of formula (I), wherein R3 is an unsaturated straight or branched $C_{2-4}$-alkenyl optionally substituted with one or more substituents.

In another preferred embodiment the invention relates to compounds of formula (I), wherein R3 is a saturated $C_{3-8}$-alicyclic hydrocarbon group optionally substituted with one or more substituents.

In another preferred embodiment the invention relates to compounds of formula (I), wherein R3 is a saturated cyclohexyl optionally substituted with one or more substituents.

In another preferred embodiment the invention relates to compounds of formula (I), wherein R3 is an aryl optionally substituted with one or more substituents.

In another preferred embodiment the invention relates to compounds of formula (i), wherein R3 is phenyl, alkoxyphenyl, dialkoxyphenyl, hydroxyphenyl, indanyl, imidazolyl, pyridyl, benzofuranyl, indolyl, benzimidazolyl, thienyl, furanyl, or pyranyl optionally substituted with one or more substituents.

In another preferred embodiment the invention relates to compounds of formula (I), wherein R3 is W optionally substituted with one or more substituents wherein W is as defined above.

In another preferred embodiment the invention relates to compounds of formula (I), wherein W is optionally substituted with one or more substituents and W is

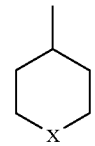

wherein X is as defined above.

In another preferred embodiment the invention relates to compounds of formula (1), wherein X is NR4 and R4 is as defined above.

In another preferred embodiment the invention relates to compounds of formula (I), wherein R4 is a saturated straight or branched $C_{1-8}$-hydrocarbon chain optionally substituted with one or more substituents or R4 is a $C_{1-8}$-acyl.

In another preferred embodiment the invention relates to compounds of formula (I), wherein R4 is methyl or methanoyl.

In another preferred embodiment the invention relates to compounds of formula (I), wherein the substituents are selected from the group consisting of halogen, hydroxyl, $C_{1-4}$-alkoxy, $C_{1-4}$-alkyl, $C_{1-4}$-alkylthio, $C_{1-4}$-alkylsulphinyl, aryl, aryloxy, hydroxyalkyl, perhalomethoxy, $C_{1-8}$-acyl, perhalomethyl, oxo, $C_{1-4}$-alkanoylamino-$C_{1-4}$-alkyl, alkoxyoxoindanyl, dimethylhydrazidyl, methylendioxy, thioxothiazolyl, imidazol, aminoalkoxy, carboxy, carboxyalkenyl, cyano or $C_{1-8}$-alkanoyloxy.

In another preferred embodiment the invention relates to compounds of formula (I), wherein the substituents are selected from the group consisting of fluorine, chlorine, bromine, hydroxyl, methoxy, ethoxy, methyl, methylthio, methylsulphinyl, furanyl, thienyl, phenyl, indolyl, pyranyl, dimethoxyphenyl, methoxyphenyl, hydroxyphenyl, hydroxymethyl, trifluoromethoxy, trifluoromethyl, imidazol, methanoyl, oxo, methanoylamino-methyl, methoxyoxoindanyl, dimethylhydrazidyl, methylendioxy, thioxothiazolyl, carboxy, cyano, acetamido, nitro, acetyl, acetyloxy, dimethylamino, 2-dimethylaminoethoxy, 2-carboxyethenyl or 2-morpholin-4-ylethoxy.

In another preferred embodiment the invention relates to compounds of formula (I), wherein R2 is COR3 and R3 is selected from the group consisting of phenyl, 3-methoxyphenyl, 4-methoxyphenyl 4-chlorophenyl, 4-trifluoromethylphenyl, 4-methylphenyl, 3,4-dimethoxyphenyl, 4-ethoxyphenyl, 4-fluorophenyl, 4-trifluoromethoxyphenyl, 4-dimethylaminophenyl, 4-bromophenyl, 4-hydroxyphenyl, 4-hydroxymethylphenyl, 4-nitrophenyl, 4-cyanophenyl, 4-methylthiophenyl, 4-methylsulfonylphenyl, 4-acetylphenyl, 4-acetamidophenyl, 4-acetoxyphenyl, 3,4-methylenedioxyphenyl, 3,4-dimethoxyphenyl, 3-chloro-4-methoxyphenyl, indolyl, 1H-indol-5-yl, and 1H-benzimidazol-5-yl, 2-(4-methoxyphenyl)-ethenyl, 2-(3-methoxyphenyl)-ethenyl, 2-(4-chlorophenyl)-ethenyl, 2-(4-fluorophenyl)-ethenyl, 2-(4-trifluoromethylphenyl)-ethenyl, 2-(4-methoxyphenyl)-ethyl, 2-(4-chlorophenyl)-ethyl, 4-chlorobenzyl, 4-methoxybenzyl, 2-(2-furyl)-ethenyl, 2-(4,5-dimethyl-2-furyl)-ethenyl, 2-(5-methyl-2-furyl)-ethenyl, 2-(3-furyl)-ethenyl, 2-(2-thienyl)-ethenyl, 2-(3-thienyl)-ethenyl, or 4-methoxyphenyl-2-ethenyl, 4-pyridyl, 5-hydroxypyrazin-2-yl, 5-chloro-6-hydroxypyridin-3-yl, 2-chloropyridin-3-yl, benzofuran-2-yl, benzothiophen-2-yl-, 7-methoxybenzofuran-2-yl, furyl, thienyl, chlorothienyl, 5-chlorothiophen-2-yl, or benzimidazol, 1H-benzimidazol-5-yl, 4-methoxycyclohexyl, 4-oxycyclohexyl, N-methylpiperidinyl, tetrahydrofuryl, tetrahydropyranyl, 4-(2-carboxyethenyl)phenyl, 4-(2-dimethylaminoethoxy)-phenyl and 4-(2-morpholin-4-ylethoxy)phenyl.

The present invention relates furthermore to a salt of a compound of formula (I) with a pharmaceutically acceptable acid or base.

The compounds according to the invention may optionally exist as pharmaceutically acceptable salts including pharmaceutically acceptable acid addition salts, such as hydrochloric, hydrobromic, hydroiodic, phosphoric, sulfuric, acetic, trifluoroacetic, trichloroacetic, oxalic, maleic, pyruvic, malonic, succinic, citric, tartaric, fumaric, mandelic, benzoic, cinnamic, methanesulfonic, ethanesulfonic, picric and the like, and include the pharmaceutically acceptable salts listed in Journal of Pharmaceutical Science, 66, 2 (1977) and incorporated herein by reference; pharmaceutically acceptable metal salts, such as lithium, sodium, potassium, or magnesium salts and the like; or—optionally alkylated—ammonium salts; or amine salts of the compounds of this invention, such as the sodium, potassium, $C_{1-8}$-alkylamine, di ($C_{1-8}$-alkyl) amine, tri ($C_{1-8}$-alkyl) amine and the corresponding omega-hydroxy analogues (e.g., methylamine, ethylamine, propylamine, dimethylamine, diethylamine, dipropylamine, trimethylamine, triethylamine, tripropylamine, di(hydroxyethyl)amine, and the like. Also intended as pharmaceutically acceptable acid addition salts are the hydrates which the present compounds are able to form. The acid addition salts may be obtained as the direct products of compound synthesis. In the alternative, the free base may be dissolved in a suitable solvent containing the appropriate acid, and the salt isolated by evaporating the solvent or otherwise separating the salt and solvent. The compounds of this invention may form solvates with standard low molecular weight solvents using methods known to the skilled artisan.

Examples of the saturated aliphatic hydrocarbon chains having 1 to 8 carbon atoms include methyl, ethyl, n-propyl, isopropyl, n-butyl, isobutyl, sec.butyl, tert.butyl, n-pentyl, isopentyl, neopentyl, tert.pentyl, n-hexyl, isohexyl and octyl. Examples of the unsaturated aliphatic hydrocarbon chains having 2 to 8 carbon atoms include ethenyl, 1-propenyl, 2-propenyl, 1-butenyl, 2-butenyl, 3-butenyl, 2-methyl-1-propenyl, I-pentenyl, 2-pentenyl, 3-pentenyl, 4-pentenyl, 3-methyl-2-butenyl, 1-hexenyl, 3-hexenyl, 2,4-hexadienyl, 5-hexenyl, ethynyl, 1-propionyl, 2-propionyl, 1-butynyl, 2-butynyl, 3-butynyl, 1-pentynyl, 2-pentenyl, 3-pentenyl, 4-pentenyl, 1-hexynyl, 3-hexynyl, 2,4-hexadiynyl, 5-hexynyl. Examples of the saturated alicyclic hydrocarbon group having 3 to 8 carbon atoms include cyclopropyl, cyclobutyl, cyclopentyl and cyclohexyl. Examples of the unsaturated $C_{1-8}$-alicyclic hydrocarbon group having 5 to 8 carbon atoms include 1-cyclopentenyl, 2-cyclopentenyl, 3-cyclopentenyl, 1-cyclohexenyl, 2-cyclohexenyl, 3-cyclohexenyl and 1-cyclooctenyl.

The term "aryl" as used herein refers to an aryl or a heteroaryl and includes phenyl, alkoxyphenyl, dialkoxyphenyl, hydroxyphenyl, biphenyl, indene, indane, fluorene, naphthyl (1-naphthyl, 2-naphthyl), anthracene (1-anthracenyl, 2-anthracenyl, 3-anthracenyl), pyrrolyl (2-pyrrolyl), pyrazolyl (e.g. 3-pyrazolyl, 4-pyrazolyl and 5-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b] furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b] thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl (2-(2,3-dihydro-benzo[b]thiophenyl), 3-(2,3-dihydro-benzo[b]thiophenyl), 4-(2,3-dihydro-benzo [b]thiophenyl), 5-(2,3-dihydro-benzo[b]thiophenyl), 6-(2,3-dihydro-benzo[b]thiophenyl), 7-(2,3-dihydro-benzo[b] thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,1 1-dihydro-5H-dibenz[b,f]azepine-1-yl, 10,11-dihydro-5H-dibenz[b,f] azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), furanyl (e.g. 2-furanyl, 3-furanyl, 4-furanyl and 5-furanyl), thienyl (e.g. 2-thienyl, 3-thienyl, 4-thienyl and 5-thienyl), tetrazolyl (5-tetrazolyl), isoxazolyl (3-isoxazolyl, 4-isoxazolyl, 5-isoxazolyl), isothiazolyl (3-isothiazolyl, 4-isothiazolyl, 5-isothiazolyl), 1,2,3-oxadiazolyl (1,2,3-oxadiazol-4-yl, 1,2,3-oxadiazol-5-yl), 1,2,3-thiadiazolyl (1,2,3-thiadiazol-4-yl, 1,2,3-thiadiazol-5-yl), 1,2,4-oxadiazolyl (1,2,4-oxadiazol-3-yl, 1,2,4-oxadiazol-5-yl), 1,2,4-thiadiazolyl (1,2,4-thiadiazol-3-yl, 1,2,4-thiadiazol-5-yl), 1,3,4-oxadiazolyl (1,3,4- oxadiazol-2-yl, 1,3,4-oxadiazol-5-yl), 1,3,4-thiadiazolyl (1,3,4-thiadiazol-2-yl, 1,3,4-thiadiazol-5-yl), 1,2,5-oxadiazolyl (1,2,5-oxadiazol-3-yl, 1,2,5-oxadiazol-5-yl),1,2,5-thiadiazolyl (1,2,5-thiadiazol-3-yl, 1,2,5-thiadiazol-5-yl), benzo[d]isoxazolyl (benzo[d]isoxazol-3-yl, benzo[d] isoxazol-4-yl, benzo[d]isoxazol-5-yl, benzo[d]isoxazol-6-yl, benzo[d]isoxazol-7-yl), benzo[d]isothiazolyl (benzo[d] isothiazol-3-yl, benzo[d]isothiazol-4-yl, benzo[d]isothiazol-5-yl, benzo[d]isothiazol-6-yl, benzo[d]isothiazol-7-yl), benzo[1,3]dioxol (benzo[1,3]dioxol-5-yl), pyranyl, N-methylpiperidinyl, tetrahydrofuryl and tetrahydropyranyl.

The term "halogen" as used herein means fluorine, chlorine, bromine or iodine.

The term "perhalomethyl" as used herein means trifluoromethyl, trichloromethyl, tribromomethyl or triiodomethyl.

The term "perhalomethoxy" as used herein means trifluoromethoxy, trichloromethoxy, tribromomethoxy or triiodomethoxy.

The term $C_{1-8}$-alkyl as used herein, refers to a straight, branched or cyclic $C_{1-8}$-hydrocarbon chain.

The term "aralkyl" as used herein refers to an optionally substituted aryl residue as defined above, connected to an optionally substituted $C_{1-6}$-alkyl as defined above. Examples of the aralkyl residue include benzyl, 2-phenylethyl, 2-phenylethenyl, 3-(2-pyridyl)propyl, 3-phenylpropyl, 1-naphtylmethyl, 2-(1-naphtyl)ethyl and the like.

The term "$C_{1-8}$-alkoxy" as used herein, alone or in combination, refers to a straight or branched monovalent substituent comprising a $C_{1-8}$-alkyl group as defined above linked through an ether oxygen having its free valence bond from the ether oxygen and having 1 to 8 carbon atoms e.g., methoxy, ethoxy, propoxy, isopropoxy, butoxy and pentoxy.

Preferred compounds of the invention are:

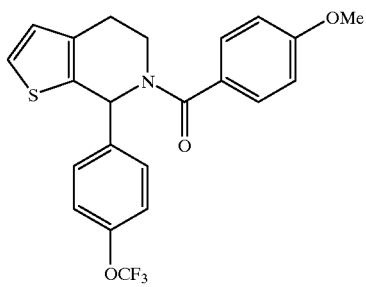

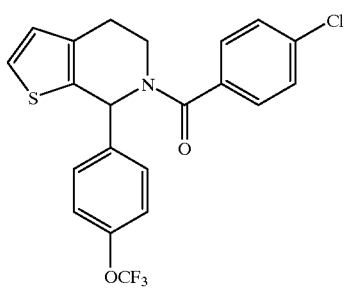

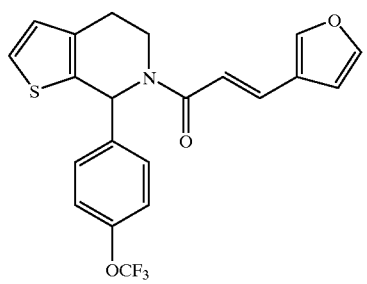

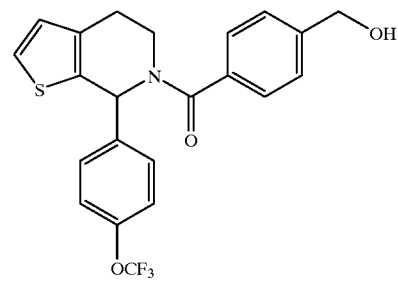

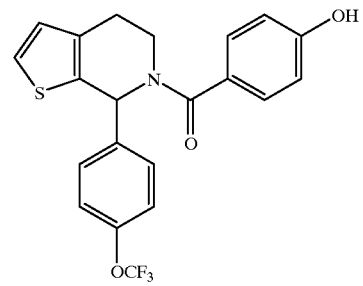

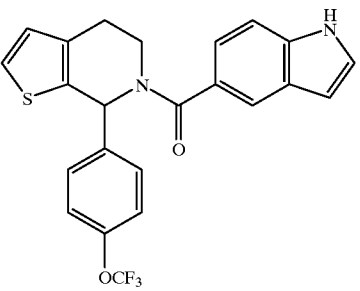

-continued
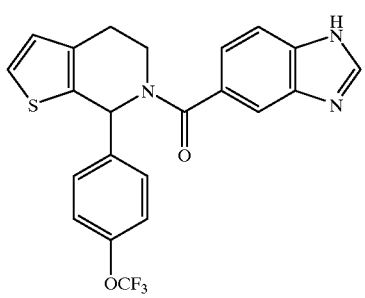
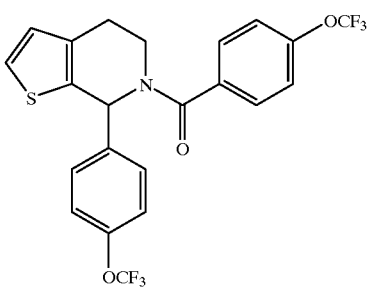
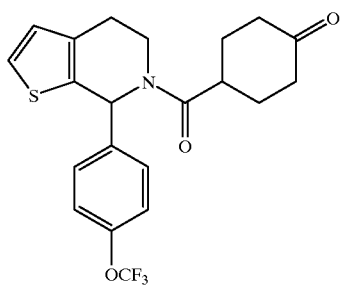
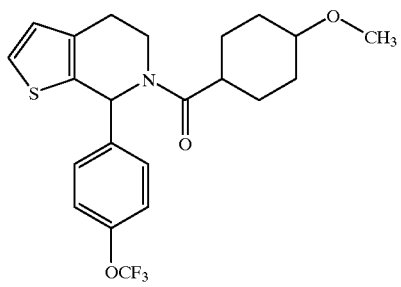
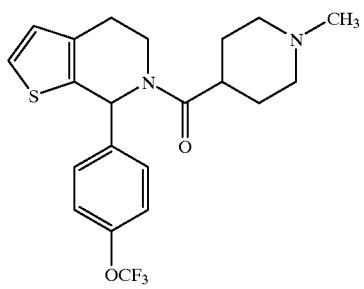
-continued
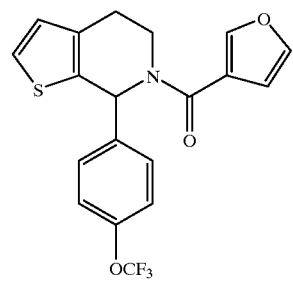
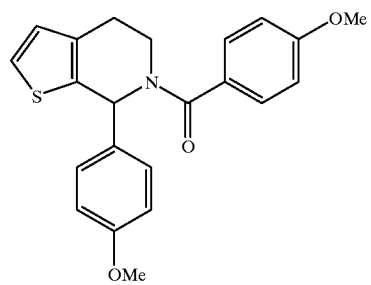
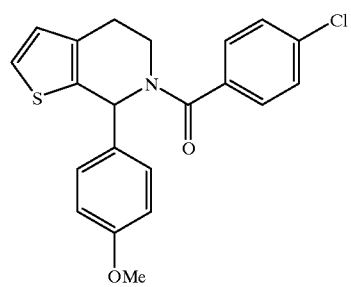
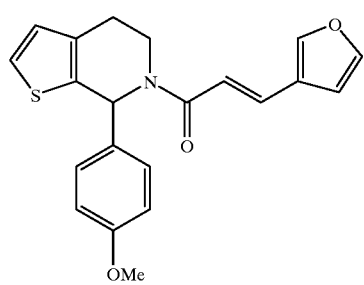
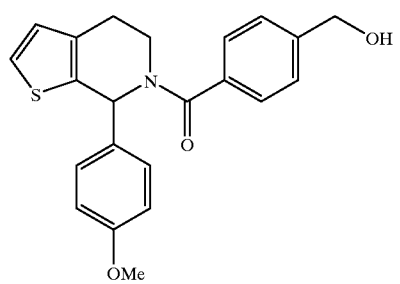
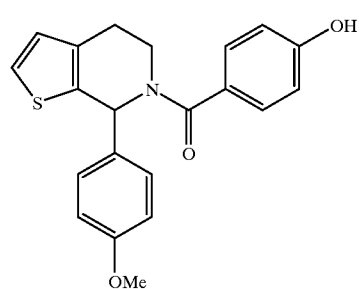

-continued
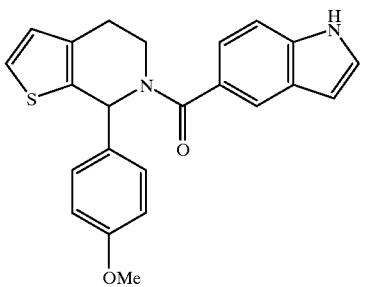
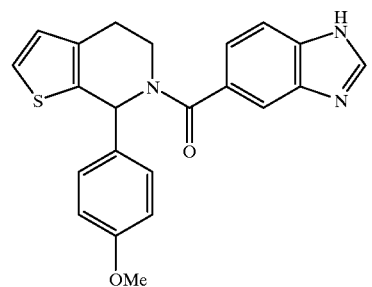
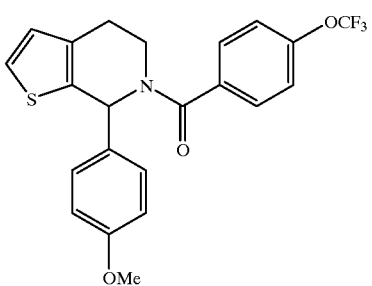
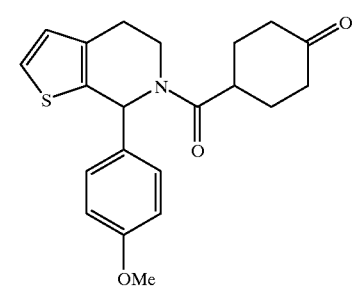
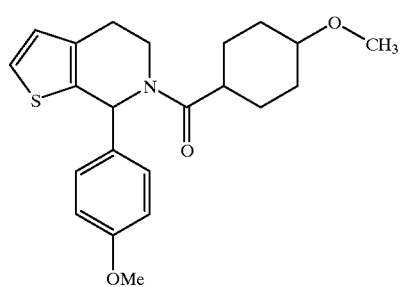
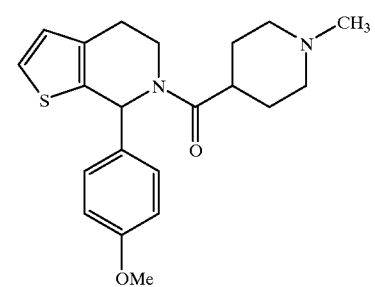
-continued
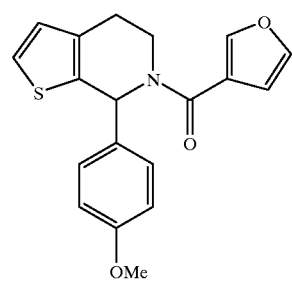
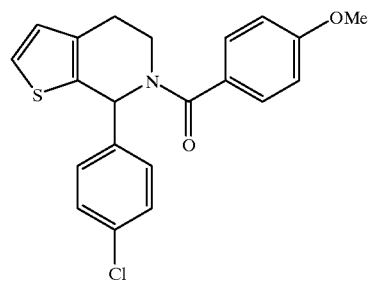
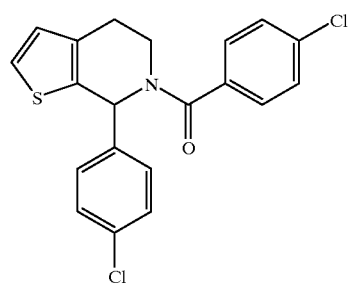
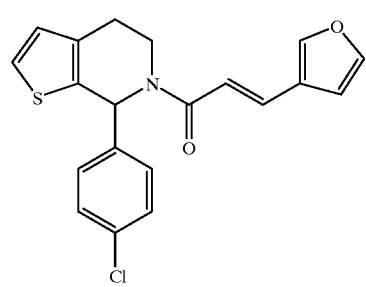
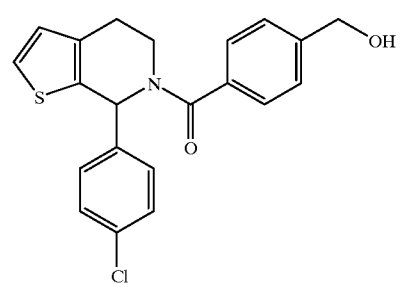
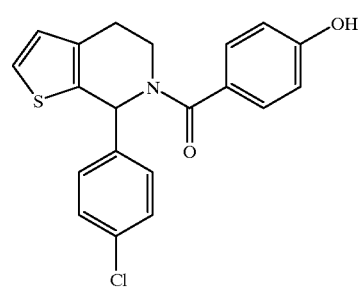

-continued
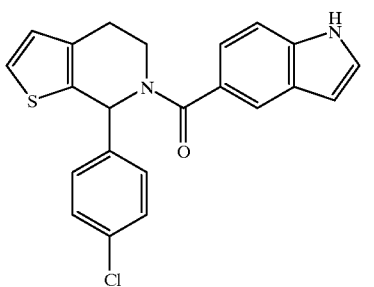
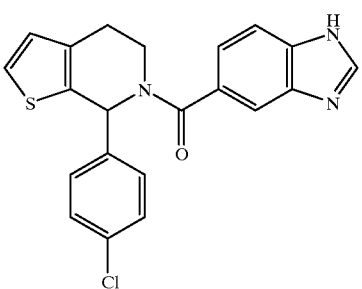
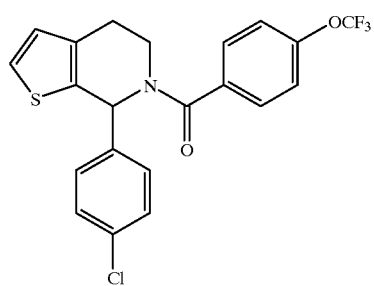
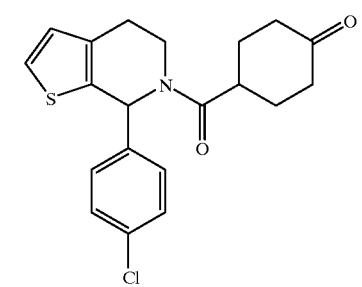
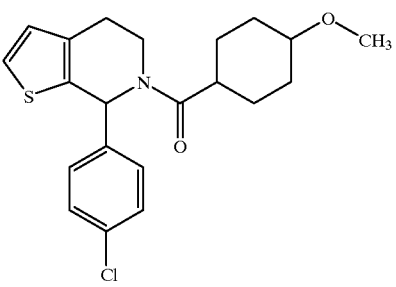
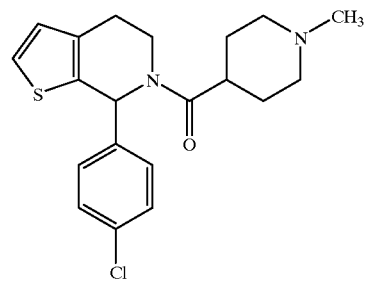
-continued
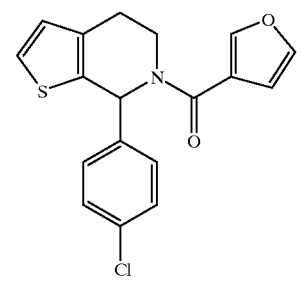
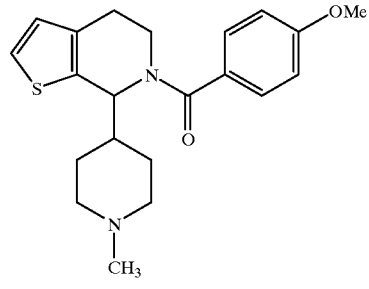
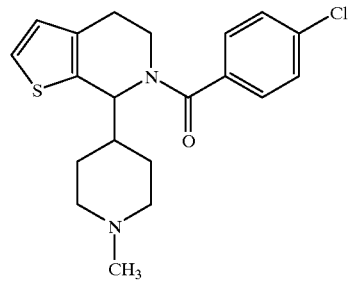
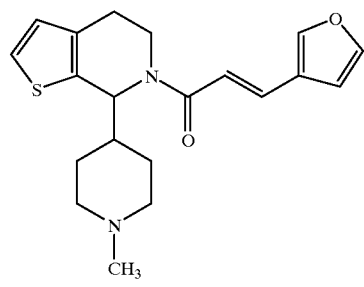
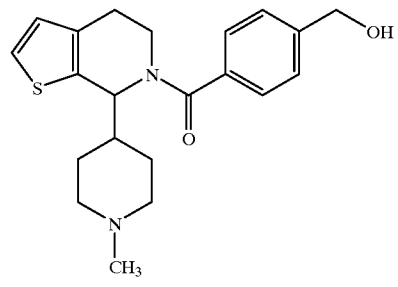
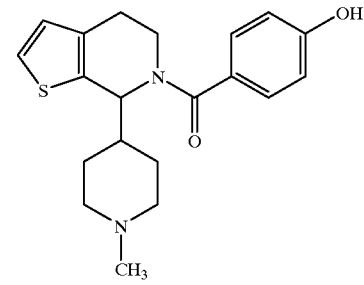

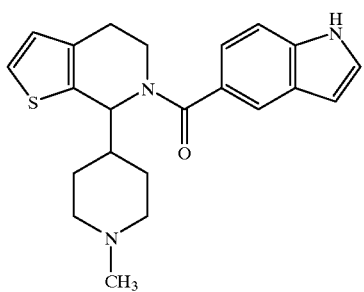
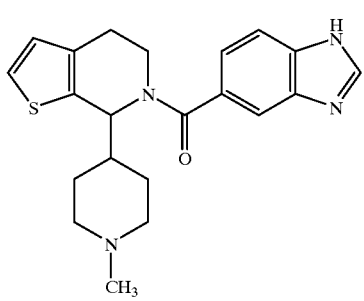
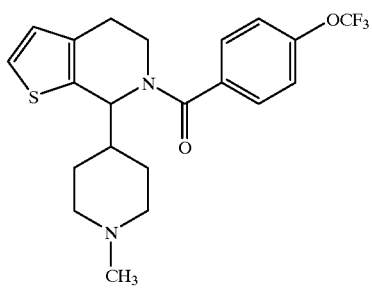
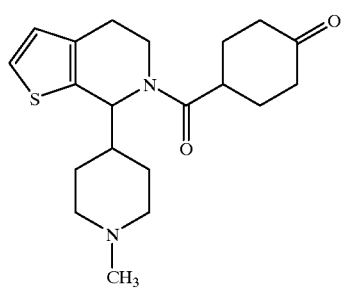
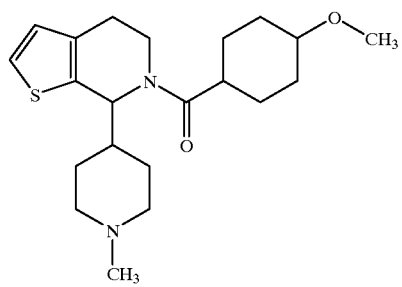
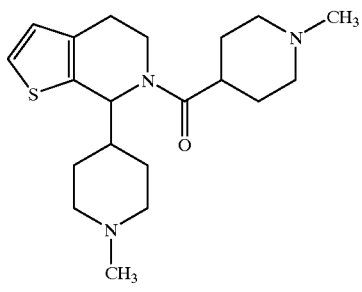
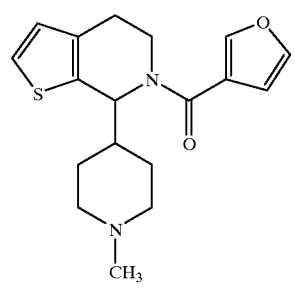
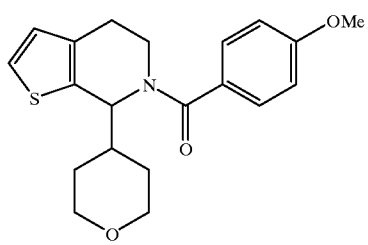
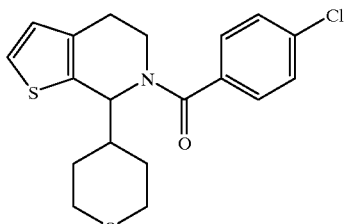
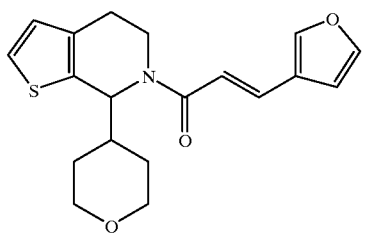
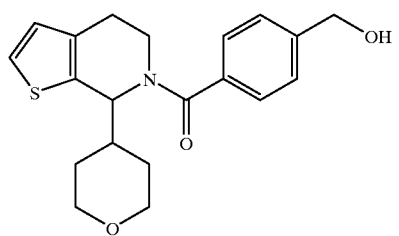

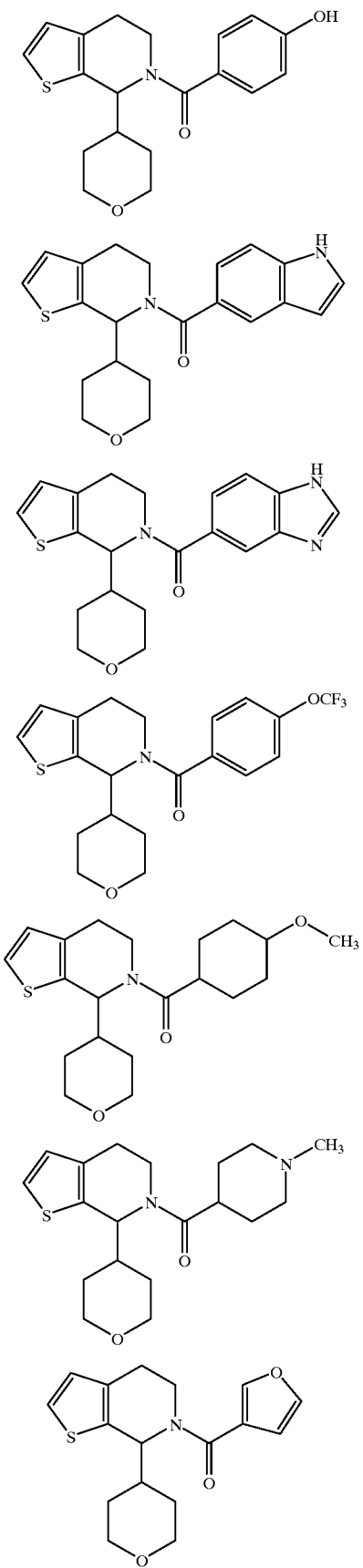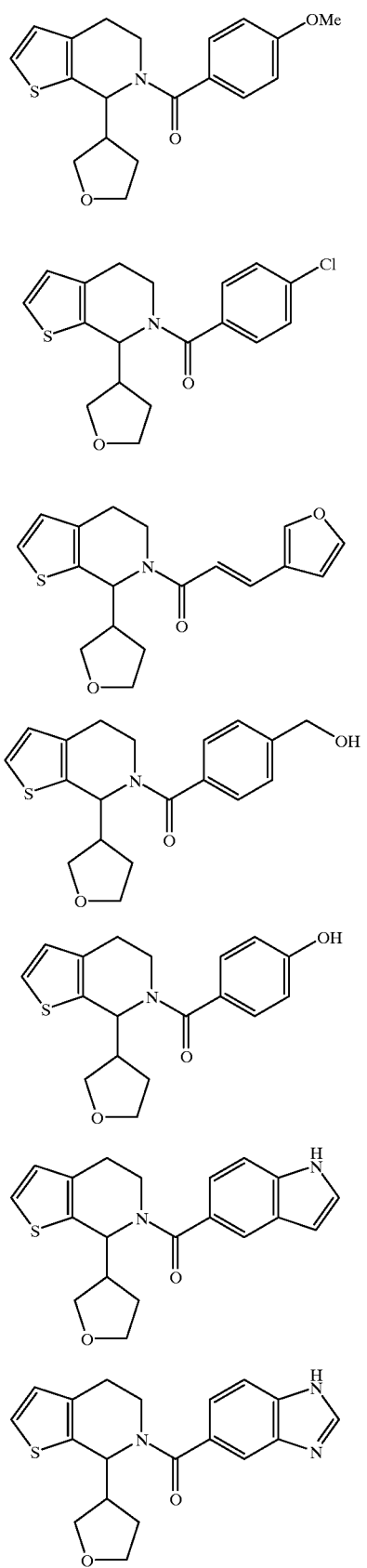

-continued
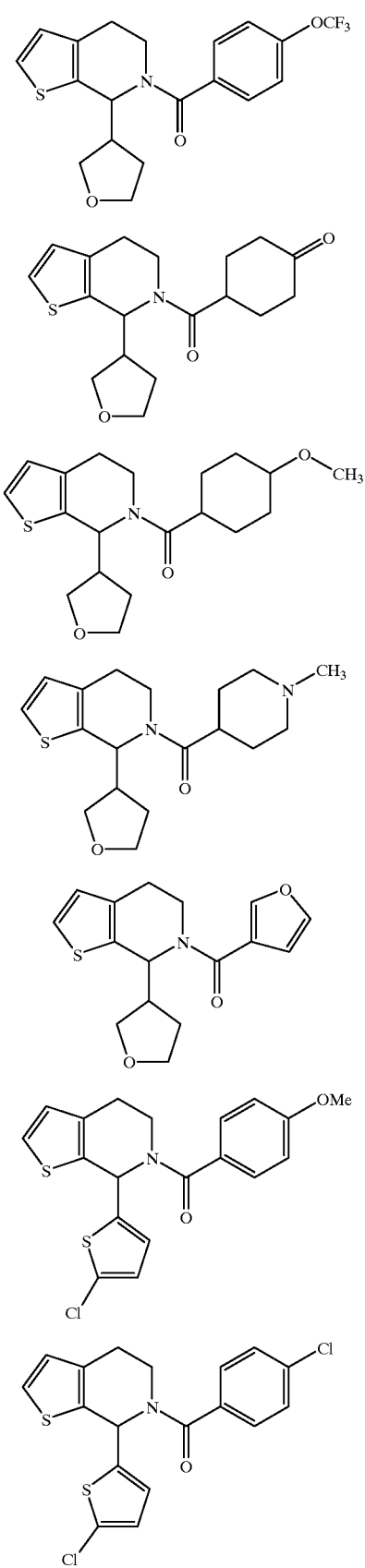
-continued
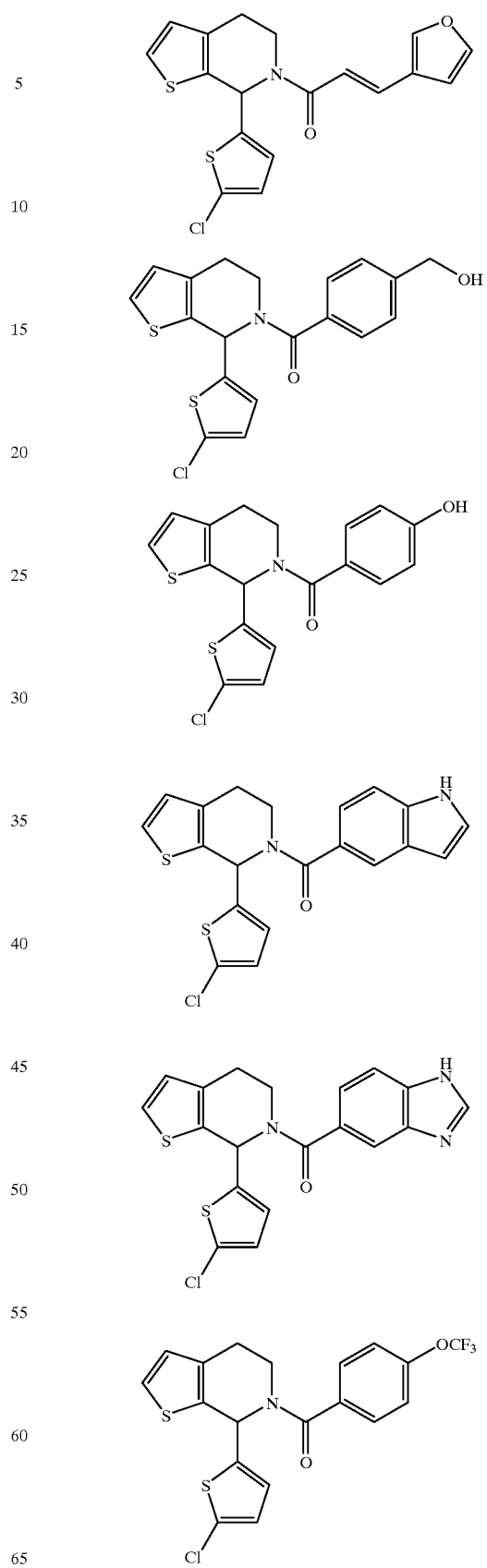

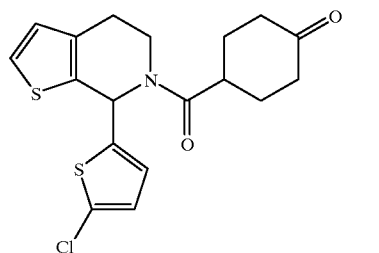
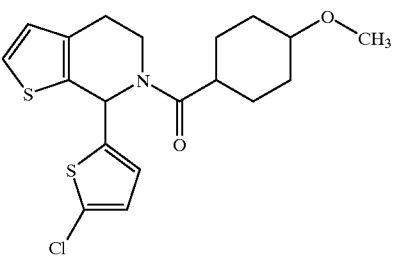
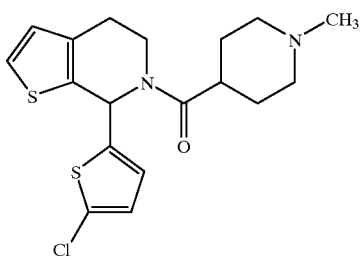
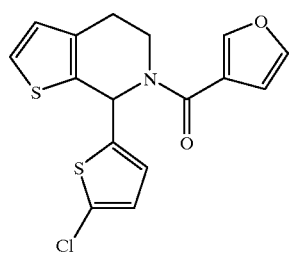
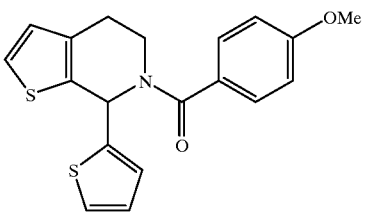
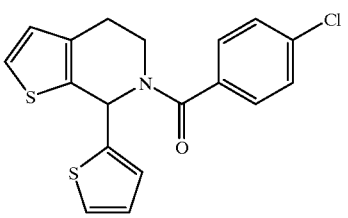
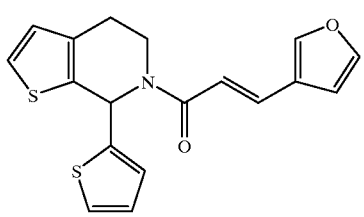
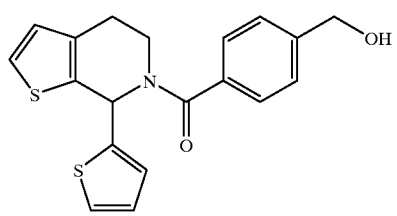
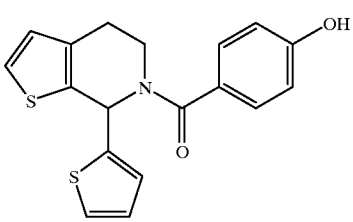
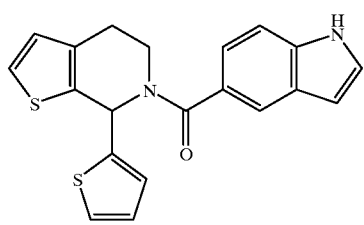
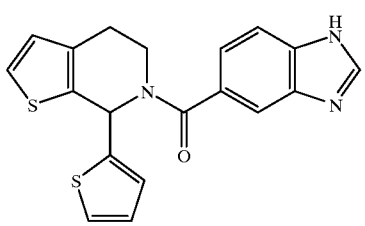
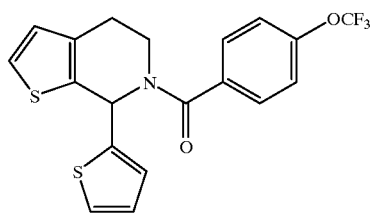
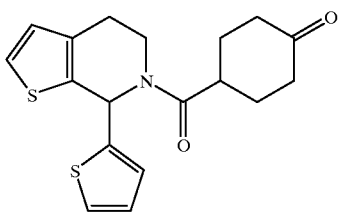
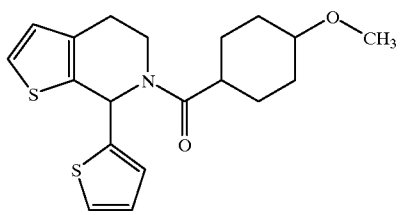

-continued
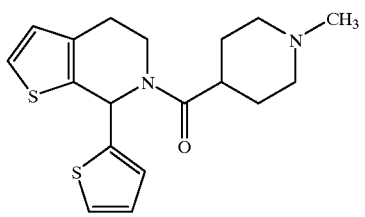
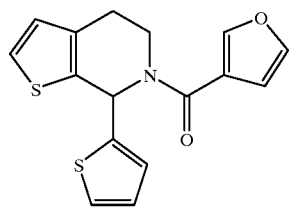
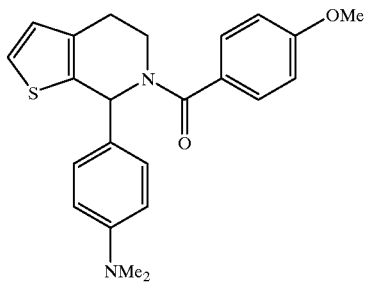
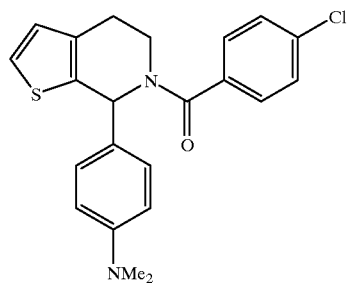
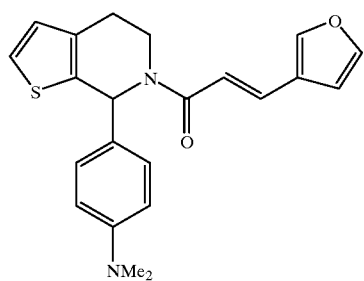
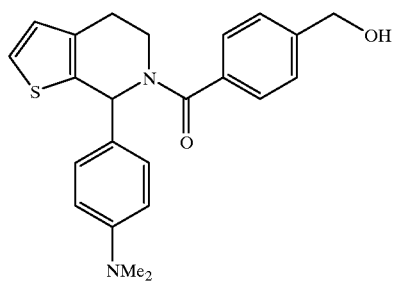
-continued
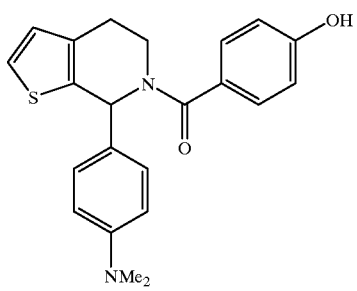
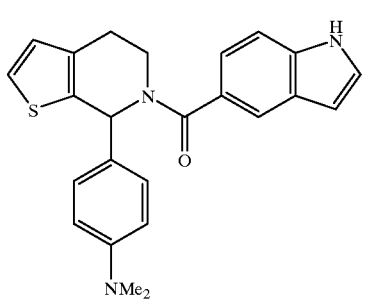
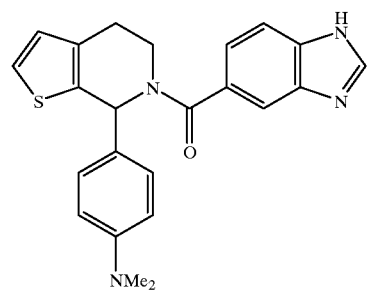
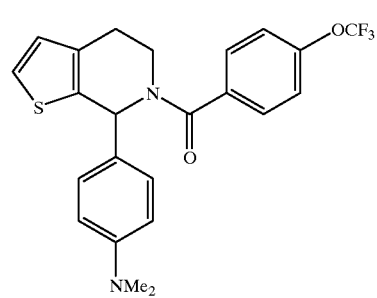
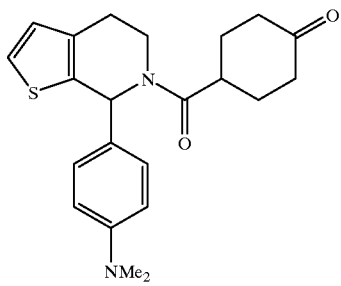

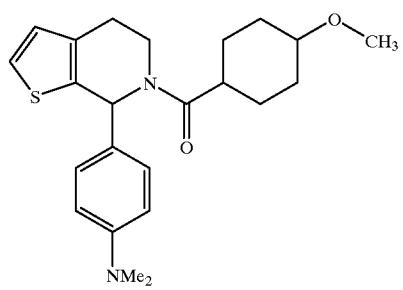
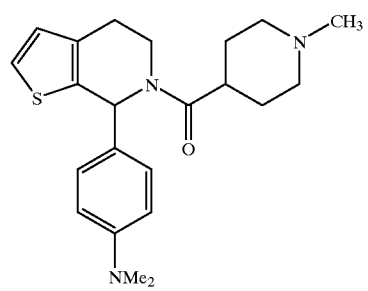
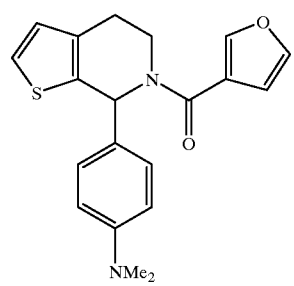
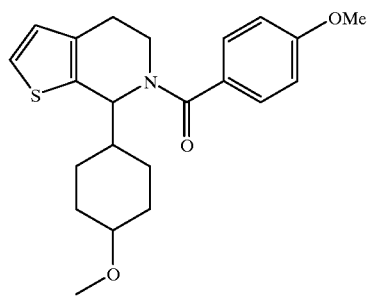
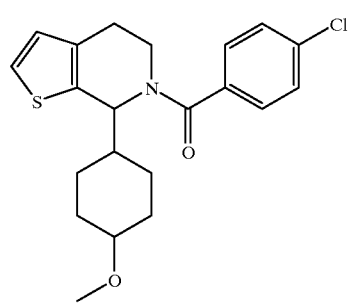
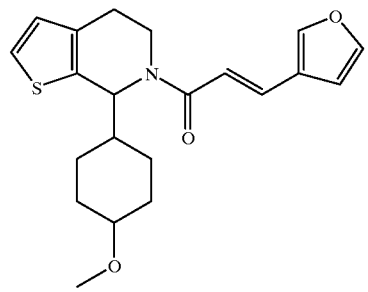
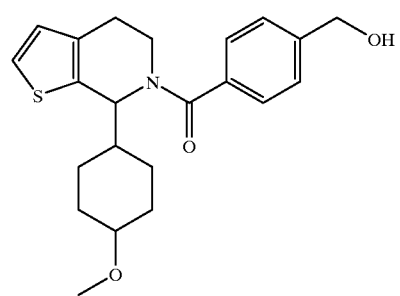
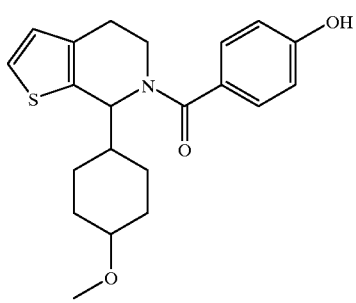
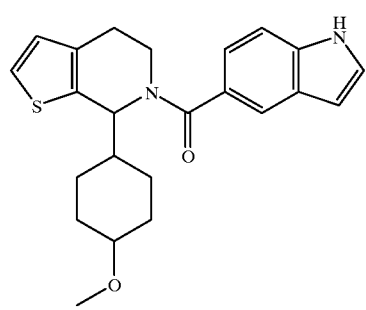
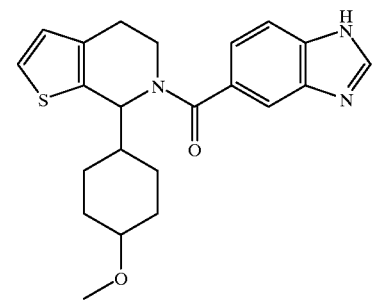

-continued
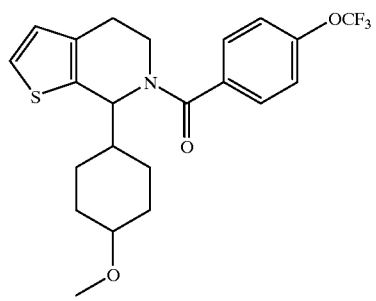
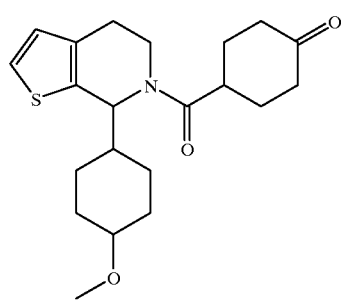
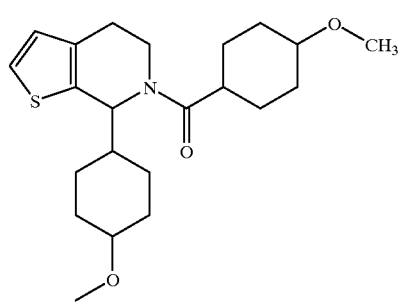
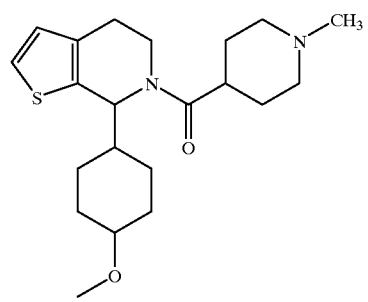
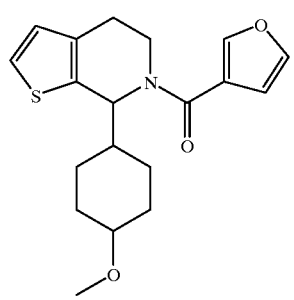
-continued
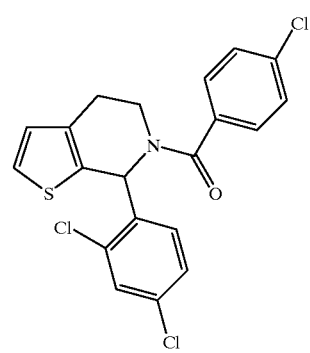
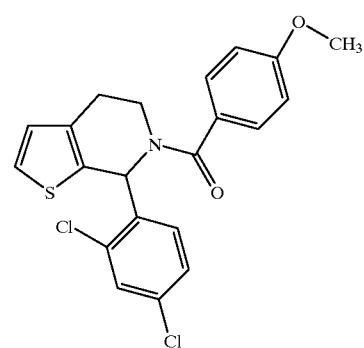
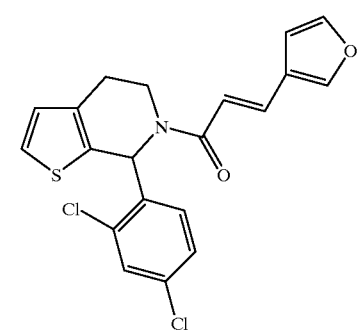
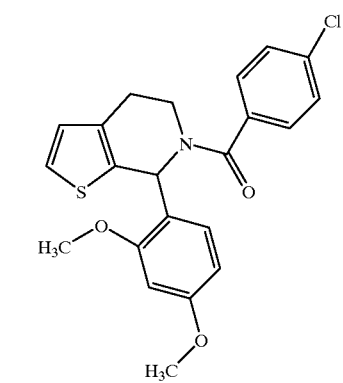

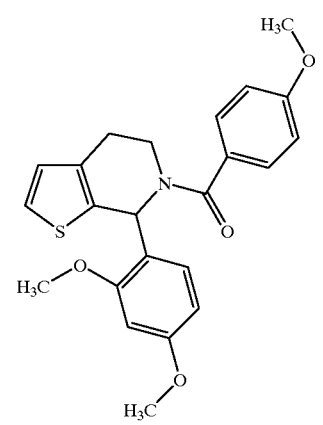
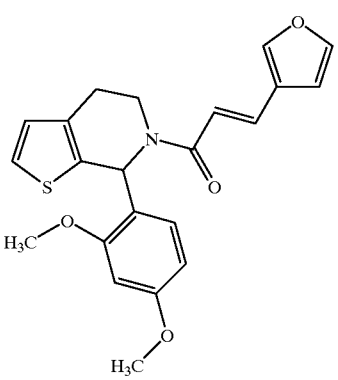
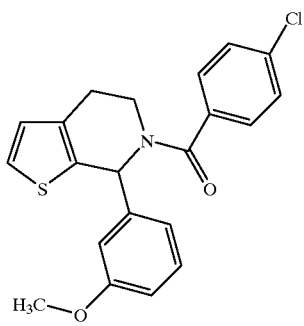
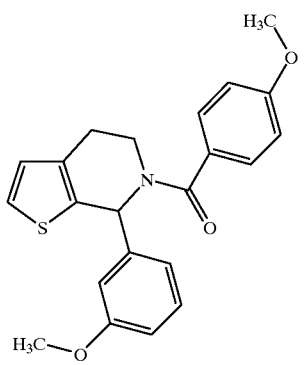
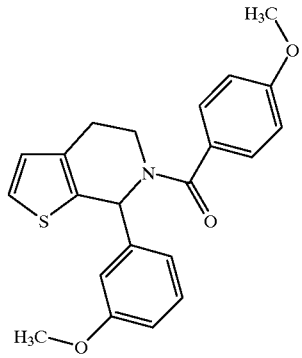
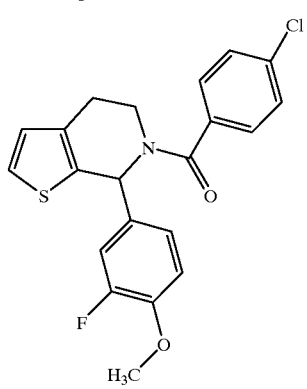
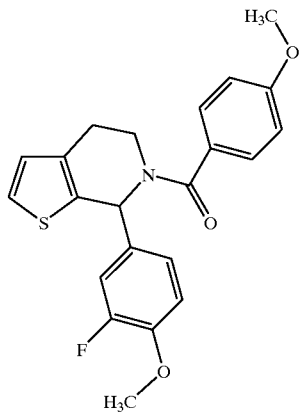
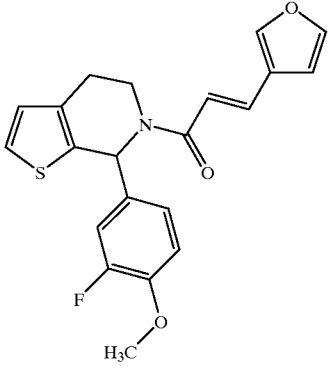

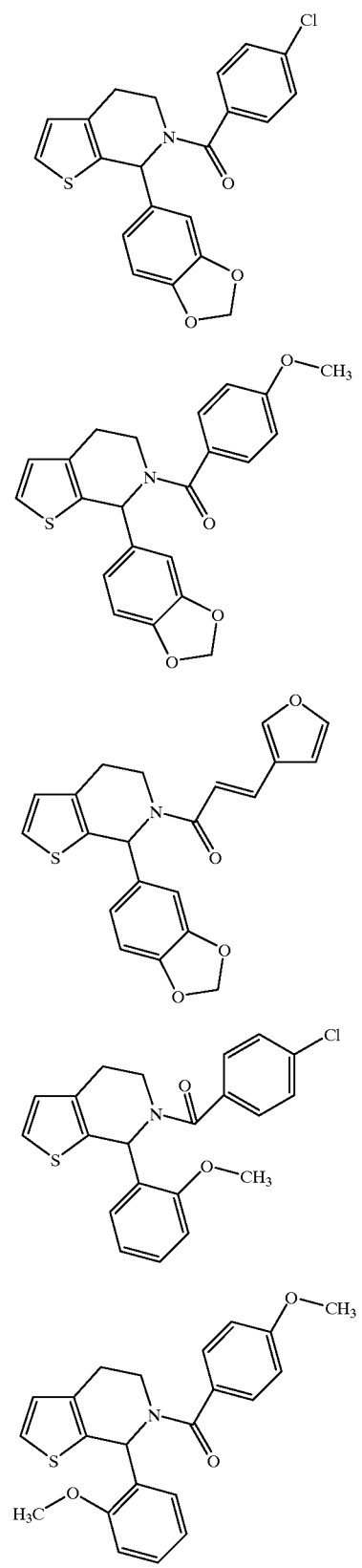
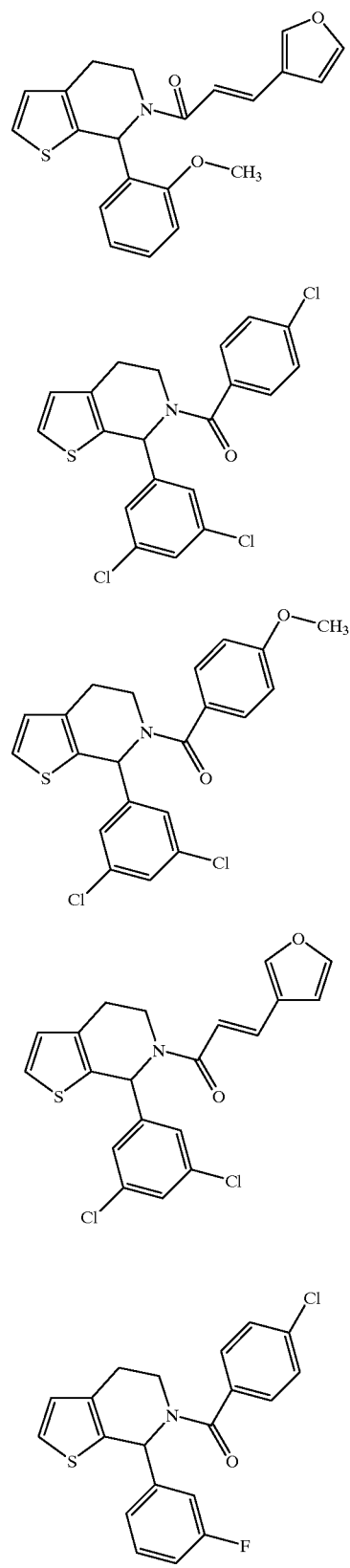

-continued

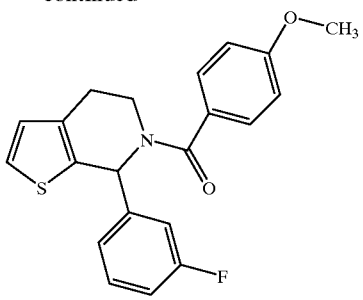

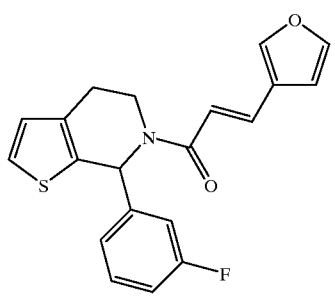

and salts there of with a pharmaceutically acceptable acid or base.

The compounds of the present invention are normoglycemic agents (i.e., compounds that are able to normalize blood glucose levels from hyper-/hypoglycemic conditions) that interact with the glucose-6-phosphatase catalytic enzyme activity, and hence make them useful in the treatment and prevention of various diseases of the endocrinologic system, especially ailments related to carbohydrate metabolism and especially the glucose metabolism, e.g. hyperglycemia, diabetes mellitus, and especially non-insulin dependent diabetes mellitus (NIDDM) including long-term complications, such as retinopathy, neuropathy, nephropathy, and micro- and macroangiopathy, and hypoglycemia resulting from, e.g., glycogen storage disease (von Gierke's Disease all types). Moreover, the present compounds are useful in the prophylactic treatment of hyperlipidemia, hypertension, liver and bile diseases, and atherosclerosis associated with diabetes. The present compounds are especially useful in the treatment of diseases associated with an increased or reduced activity of the glucose-6-phosphatase complex, e.g. the G-6-Pase catalytic enzyme.

Accordingly, in another aspect the invention relates to a compound of formula (I) or a pharmaceutically acceptable salt thereof with a pharmaceutically acceptable acid or base, or any optical isomer or mixture of optical isomers, including a racemic mixture, or any tautomeric form for therapeutic use. Preferably for treatment or prevention of diseases of the endocrinologic system, preferably hyperglycemia or diabetes.

Furthermore, the invention also relates to the use of a compound of formula (I) or a pharmaceutically acceptable salt thereof with a pharmaceutically acceptable acid or base, or any optical isomer or mixture of optical isomers, including a racemic mixture, or any tautomeric form for the preparation of a medicament.

Furthermore, the invention also relates to the use of a compound of formula (I) or a pharmaceutically acceptable salt thereof with a pharmaceutically acceptable acid or base, or any optical isomer or mixture of optical isomers, including a racemic mixture, or any tautomeric form for the preparation of a medicament for the treatment or prevention of diseases of the endocrinologic system, preferably hyperglycemia or diabetes.

Furthermore, the invention also relates to the use of a compound of the general formula (I) or a pharmaceutically acceptable salt thereof with a pharmaceutically acceptable acid or base, or any optical isomer or mixture of optical isomers, including a racemic mixture, or any tautomeric form for the preparation of a medicament for the treatment or prevention of glycogen storage disease or hypoglycaemia.

The invention relates furthermore to a method of treating or preventing diseases of the endocrinologic system, preferably hyperglycemia or diabetes in a subject in need thereof comprising administering an effective amount of a compound of formula (I) to said subject.

Methods

The compounds of the invention can be prepared by the following methods:

a)
Reacting a compound of formula II with a compound of structure III under formation of a compound of structure IV according to the following reaction scheme.

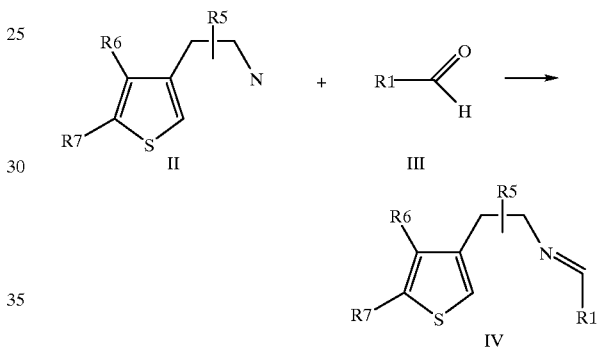

R1, R5, R6, and R7 are as defined above.

Compounds of formula I(can conveniently be prepared from purchasable compounds using methods described in the literature, e.g., M. Cardellini et al. Eur. J. Med. Chem. (1994) 29, 423–429.

b)
Reacting a compound of formula IV with an agent A capable of introducing a ring closure forming a compound of structure V according to the reaction scheme below.

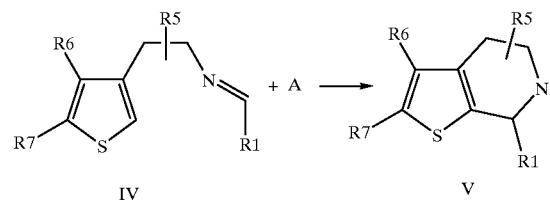

Agents which can introduce ring closure could be chosen from trifluoroacetic acid, phosphoroxy chloride, phosphorpentoxide, sulfuric acid, methanesulphonic acid, mixtures thereof, or other agents known in the art.

R1, R5, R6 and R7 are as defined above.

c)
Reacting a compound of formula V with a compound of formula R2—L under formation of a compound of formula I according to the reaction scheme below.

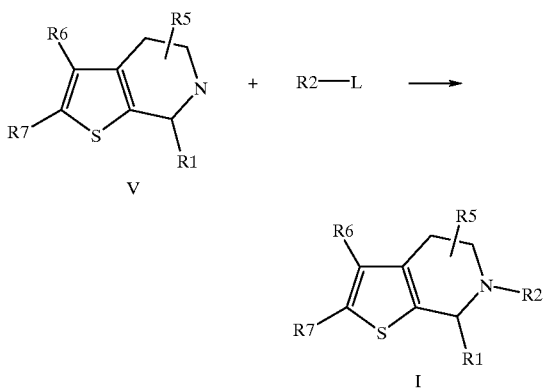

R1, R2, R5, R6 and R7 are as defined above.

L is a good leaving group such as halogen, sulfate, sulfonate or acyl; when R2 is R3CO— where R3 is as defined above, L can be selected from fluorine, chlorine, bromine, iodine, 1-imidazolyl, 1,2,4-triazolyl, 1-benzotriazolyloxy, 1-(4-aza benzotriazolyl)oxy, pentafluorophenoxy, N-succinyloxy 3,4-dihydro-4-oxo-3-(1,2,3-benzotriazinyl)oxy, R3COO—, or any other leaving group known to act as a leaving group in acylation reactions. A base can be either absent (i.e. compound V acts as a base) or triethylamine, N-ethyl-N,N-diisopropylamine, N-methylmorpholine, 2,6-lutidine, 2,2,6,6-tetramethylpiperidine, potassium carbonate, sodium carbonate, caesium carbonate or any other base known to be useful in acylation reactions. R3CO—L can be prepared by activation of the corresponding carboxylic acid in the presence or absence of the alcohol component of the activated ester, such as HOBt, HOAt, HOSu, HOPFP, using various carbodiimide reagents, such as dicyclohexyl- or diisopropylcarbodiimide, EDAC and the like, or using phosphorous based activation reagents, such as PyBOP, PyBrOP, TFFH and the like, carbonyldi-azole reagents such as carbonyldiimidazole, carbonyldi-1,2,4-triazole, or any other activation or coupling reagent known to those skilled in the art.

Compounds of formula V can also be prepared by the following reactions.

d)

Reacting a compound of formula II with a compound of formula VI to form a compound of formula VII as shown in the reaction scheme below.

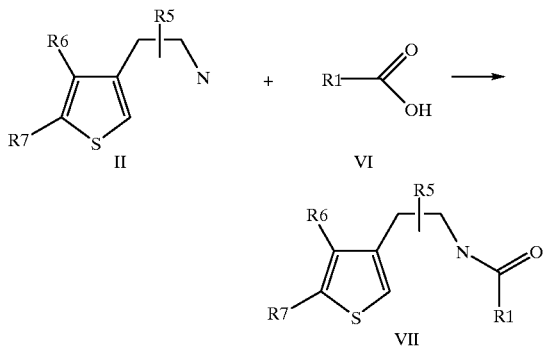

R1, R5, R6 and R7 are as defined above.

The reaction can conveniently be carried out by activation of the carboxylic acid with agents such as HOBt, HOAt, HOSu, HOPFP, using various carbodiimide reagents, such as dicyclohexyl- or diisopropylcarbodiimide, EDAC and the like, or using phosphorous based activation reagents, such as PyBOP, PyBrOP, TFFH and the like, carbonyldi-azole reagents such as carbonyldiimidazole, carbonyldi-1,2,4-triazole, or any other activation or coupling reagent known to those skilled in the art.

e)

Reacting a compound of formula VII with an agent A capable of introducing ring closure under formation of a compound of structure IIX as depicted in the reaction scheme below.

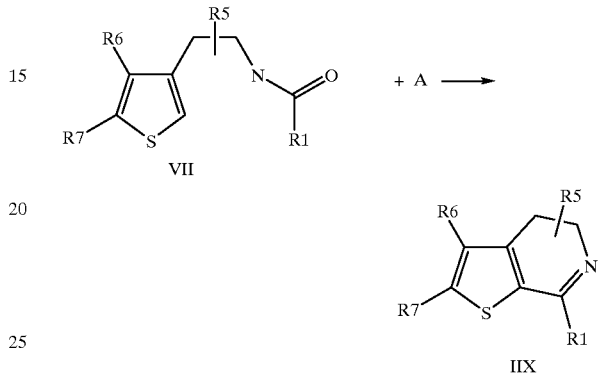

R1, R5, R6 and R7 are as defined above, A being an agent which can introduce ring closure such as trifluoroacetic acid, phosphoroxy chloride, phosphorpentoxide, sulfuric acid, methanesulphonic acid, or other acids, or anhydrides or mixtures thereof or other agents capable of introducing ring closure under water absorption known in the art.

f)

Reacting a compound of formula IIX with a reducing agent under formation of a compound structure V.

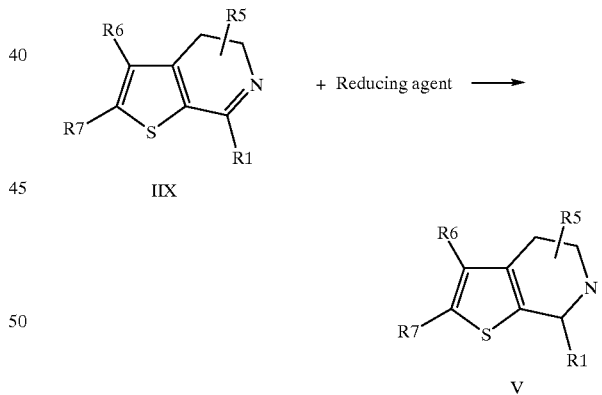

R1, R5, R6 and R7 are as defined above.

The reducing agent can be chosen from sodium borohydride, lithium aluminium hydride, lithium triethylborohydride, aluminium hydride and other reducing agents known in the art.

Or the compounds of formula (I) may be prepared by art-recognized procedures from known compounds or readily preparable intermediates.

Examples of the methods which can be used for the synthesis of the starting materials and intermediates for the compounds of the invention can be found in, e.g., S. Gronowitz and E. Sandberg, *Ark. Kemi,* 1970, 32,217–227;

G. Wolf and F. Zymalkowski, *Arch. Pharm. (Weinheim)* 1976, 309, 279–288.

E. J. Browne, *Aust. J. Chem.,* 1984, 37, 367–379.

Tupper D. E. et al., *J. Heterocyclic Chem.,* 33, 1123–9 (1996), Stokker G. E., *Tetrahedron Lett.,* 37, 5453–6 (1996), Nakagawa, M. et al., *Chem. Pharm. Bull.,* 41, 287–91 (1993), Singh H. et al., *Heterocycles,* 23, 107–10 (1985), Skinner W. A. et al., *Can. J. Chem.,* 43, 2251–3 (1965). P. Kumar et al., *J. Heterocyclic Chem.,* 19, 677–9 (1982), L. K. Lukanov et al., *Synthesis,* 1987, 204–6, A. L. Stanley & S. P. Stanforth, *J. Heterocyclic Chem.,* 31, 1399–1400 (1994), A. K. Bose et al., *J. Org. Chem.,* 56, 6968–70 (1991), K. Kementani et al., *Heterocycles,* 3, 311–41 (1975), E. Domonguez et al., *Tetrahedron,* 43, 1943–8 (1987), J. B. Bremner et al., *Aust. J. Chem.,* 41, 1815–26 (1988), M. J. O'Donnel et al., *Tetrahedron. Lett.,* 23, 4259–62 (1982).

Pharmacological methods

The ability of compounds to inhibit glucose-6-phosphatase (G-6-Pase) catalytic enzyme activity from pig liver microsomes was tested in the following way:

Pig liver microsomes were prepared in a buffer containing 250 mM sucrose, 1 mM EDTA, 25 mM HEPES and 250 mg/l Bacitrazin (pH 7.5) essentially as described by Arion et al., 1980 (Arion, Lange, & Walls. 1980). Microsomes were kept at −80° C. until use.

Prior to measurement microsomes were treated with Triton X-100 (0.04%) ("disrupted microsomes"). G-6-Pase activity was assayed for 6 min at 30° C. in a total volume of 325 µL containing 0.5 mM glucose-6-phosphate, 30 mM MES (pH 6.5), test compound and disrupted microsomes (0.05 mg). The reaction was terminated by addition of 100 µL Sigma phosphorus reagent (cat no 360-3C). This mixture was allowed to stand for 2 min, where the absorbance (A) was measured at 340 nm. All values were corrected for blank. The inhibitory effect was expressed as percent of control value, i.e., $IC_{50}$ is the concentration of a compound that produces 50% inhibition.

The compounds of the invention are preferably characterized by having a glucose-6-phosphatase inhibitory activity corresponding to an $IC_{50}$ value of less than 100 µM, more preferably less than 10 µM, even more preferably less than 1 µM, still more preferably less than 100 nM.

The compounds according to the invention are effective over a wide dosage range. In general satisfactory results are obtained with dosages of from about 0.05 to about 1000 or 5000 mg, preferably from about 0.1 to about 500 mg, per day. A most preferable dosage is about 5 mg to about 200 mg per day. The exact dosage will depend upon the mode of administration, form in which the compound is administered, the subject to be treated and the body weight of the subject to be treated, and the preference and experience of the physician or veterinarian in charge.

The present invention relates furthermore to a pharmaceutical composition comprising, as an active ingredient, a compound of formula (I) or a pharmaceutically acceptable salt thereof with a pharmaceutically acceptable acid or base, or any optical isomer or mixture of optical isomers, including a racemic mixture, or any tautomeric form together with one or more pharmaceutically acceptable carriers or diluents.

The dosage unit of the pharmaceutical compositions according to the invention typically contains from 0.05 mg to 1000 mg, preferably from 0.1 mg to 500 mg, or, preferably from 5 mg to 200 mg per day of the active ingredient, which is, preferably, a novel 4,5,6,7-tetrahydro-thieno[2,3-c]pyridine derivative as described herein or a pharmaceutically acceptable salt thereof with a pharmaceutically acceptable acid or base, or any optical isomer or mixture of optical isomers, including a racemic mixture, or any tautomeric form thereof; or the active ingredient is a previously described 4,5,6,7-tetrahydro-thieno[2,3-c]pyridine derivative or a pharmaceutically acceptable salt thereof with a pharmaceutically acceptable acid or base, or any optical isomer or mixture of optical isomers, including a racemic mixture, or any tautomeric form thereof.

The route of administration may be any route, which effectively transports the active compound to the appropriate or desired site of action, such as oral, nasal, pulmonary, transdermal or parenteral, e.g., rectal, depot, subcutaneous, intravenous, intraurethral, intramuscular, intrapulmonary, intranasal, ophthalmic solution or an ointment, the oral route being preferred.

Optionally, the pharmaceutical composition of the invention may comprise a compound of formula I combined with one or more compounds exhibiting a different activity, e.g., a plasma lipid lowering compound, a sulphonylurea like compound, or other oral agents useful in the treatment of diabetes, or other pharmacologically active material.

Pharmaceutical compositions containing a compound of the present invention may be prepared by conventional techniques, e.g., as described in *Remington: The Science and Practice of Pharmacy,* $19^{th}$ Ed., 1995. The compositions may appear in conventional forms, such as, for example, capsules, tablets, aerosols, solutions, suspensions or topical applications.

Typical compositions include a compound of formula (I) or a pharmaceutically acceptable acid addition salt or metal salt thereof, associated with a pharmaceutically acceptable excipient which may be a carrier or a diluent or be diluted by a carrier, or enclosed within a carrier which can be in form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampule, capsule, sachet, paper, or other container. When the carrier serves as a diluent, it may be solid, semi-solid, or liquid material which acts as a vehicle, excipient, or medium for the active compound. The active compound can be adsorbed on a granular solid container, for example, in a sachet. Some examples of suitable carriers are water, salt solutions, alcohols, polyethylene glycols, polyhydroxyethoxylated castor oil, gelatin, lactose, amylose, magnesium stearate, talc, silicic acid, fatty acid monoglycerides and diglycerides, pentaerythritol fatty acid esters, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavoring agents. The formulations of the invention may be formulated in any galenic dosage form so as to provide quick, sustained, or delayed release of the active ingredient after administration to the patient by employing procedures well-known in the art. The pharmaceutical preparations can be sterilized and mixed, if desired, with auxiliary agents, emulsifiers, salt for influencing osmotic pressure, buffers and/or coloring substances and the like, which do not deleteriously react with the active compounds.

For administration, preferably nasal administration, the preparation may contain a compound of formula (I) dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabens. For parenteral application, particularly suitable are injectable solutions or suspensions, preferably aqueous solutions with the active compound dissolved in polyhydroxylated castor oil. Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet, appropriate for use in this method, may be prepared by conventional tabletting techniques and contains:

| Core: | |
|---|---|
| Active compound (as free compound or salt thereof) | 5.0 mg |
| Colloidal silicon dioxide (AEROSIL) | 1.5 mg |
| Cellulose, microcryst. (AVICEL) | 70 mg |
| Modified cellulose gum (AC-DI-SOL) | 7.5 mg |
| Magnesium stearate | Ad. |
| Coating: | |
| HPMC approx. | 9 mg |
| *MYWACETT 9-40 T approx. | 0.9 mg |

*Acylated monoglyceride used as plasticizer for film coating.

Due to their high degree of activity, the compounds of the invention may be administered to a mammal in need of such treatment, prevention, elimination, alleviation or amelioration of various diseases as mentioned above and especially of diseases of the endocrinologic system such as hyperinsulinemia and diabetes. Such mammals include both domestic animals, e.g. household pets, and non-domestic animals such as wildlife. Preferably the mammal is a human.

EXAMPLES

The processes for preparing compounds of formula (I) and preparations containing them is further illustrated in the following examples which are not to be construed as limiting.

Example 1
Preparation of [7-(4-trifluoromethoxyphenyl)-4,5,6,7-tetrahydro-thieno[2,3-c]pyridin-6-yl]-(4-methoxyphenyl)methanone

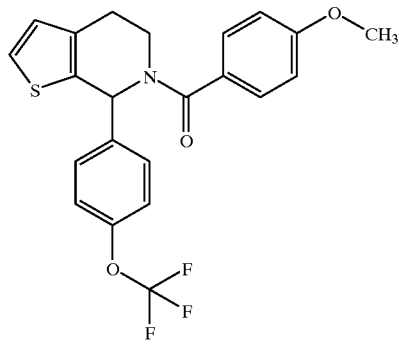

A solution of 2-(3-thienyl)ethylamine (14.7 g, 0.115 mol) and 4-trifluormethoxybenzaldehyde (15.0 g, 0.08 mol) in benzene (200 ml) was refluxed (Dean-Stark trap, $H_2O$ removed) for 4 h. Trifluoroacetic acid (2 ml) was added and the mixture was refluxed for 8 h. After cooling it was made alkaline with $NH_4OH$ and washed with water. The organic phase was dried ($K_2CO_3$) and evaporated in vacuo to give a residue, which was purified by chromatography on silica gel (200 g). A by-product was removed by elution with benzene, $R_F$=0.68 ($SiO_2$; $CHCl_3$/EtOH/$NH_4OH$=200:10:1), probably Schiff base (it was decomposed by an attempt to prepare hydrogen oxalate). The crude title base (3.9 g) was obtained by elution with chloroform.

$R_F$=0.47 ($SiO_2$; $CHCl_3$/EtOH/$NH_4OH$=200:10:1).

Hydrogen oxalate: It was prepared by neutraliZation of solution of above base in diethyl ether with a solution of oxalic acid dihydrate in acetone. Hydrogen oxalate was contaminated with hydrogen oxalate of 2-(3-thienyl)ethylamine. A suspension of the mixture was repeatedly boiled with water and filtrated. This afforded, after drying, pure 4-(4-trifluoromethoxyphenyl)-4,5,6,7-tetrahydrothieno[2,3-c]pyridine, hydrogen oxalate 2.5 g (8%), m.p. 190–195° C.

$^1$H NMR (250 MHz. DMSO-$d_6$, $\delta_H$): 9.22 (s, 3H); 7.59 (d, J=8.6 Hz, 2H); 7.47 (d, J=4.9 Hz, 1H); 7.42 (d, J=8.6 Hz, 2H); 6.97 (d, J=4.9 Hz, 1H); 5.73 (s, 1H); 3.35 (bm, 2H); 2.95 (bm, 2H).

Calculated for $C_{14}H_{12}F_3NOS$, $C_2H_2O_4$, ¼$H_2O$: C, 48.79%; H, 3.71%; N, 3.56%; F, 14.47%, S, 8.14%; Found: C, 48.69%; H 3.60%; N, 3.42%; F, 14.83%, S, 8.38%.

4-Methoxybenzoic acid (0.1 g, 0.67 mmol) was dissolved in DMF (2 ml) and 1-hydroxybenzotriazole (0.12 g, 0.8 mmol) was added followed by EDAC (0.15 g, 0.8 mmol). The resulting mixture was stirred at room temperature for 30 minutes and then the above 7-(4-trifluormethoxyphenyl)-1,2,3,4-tetrahydrothieno[2,3-c]pyridine as free base (0.24 g, 0.8 mmol) was added and the resulting mixture was stirred at room temperature for 16 hours. Ethyl acetate (15 ml) was added and the mixture was washed with water (3×10 ml), dried over $MgSO_4$ and concentrated in vacuo. The residue was purified by preparative TLC eluting with a mixture of ethyl acetate and heptane (1:3). This afforded 0.09 g (31%) of the title compound. HPLC-MS: $R_t$=16.5 min. m/z: 434 (M+1)

Example 2
[7-(4-Chloro-phenyl)-4,5,6,7-tetra hydrothieno[2,3-c]pyridin-6-yl]-(4-methoxy-phenyl)-methanone

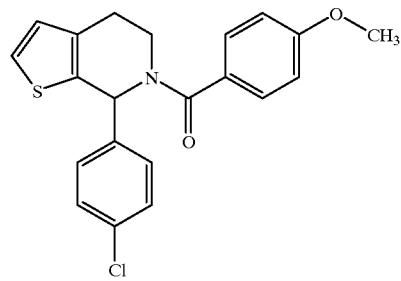

2-(3-Thienyl)ethanamine was prepared analogous to the method described by M. Cardellini et al.

Thiophene-3-carboxaldehyde (15.0 g), nitromethane (9.79 g) and sodium methoxide (2 M, 71.25 ml) were mixed in methanol (dry, 50 ml).

The mixture was stirred at room temperature for 2 h, dry diethyl ether (60 ml) was added, the mixture filtered and the isolated crystalline mass dried in vacc.

Subsequently the crystals were added to a mixture of HCl (2 N, 1 L) and toluene (1.5 L).

The mixture is stirred for 30 min and the organic phase was separated, dried over MgSO4 filtered and evaporated to dryness.

The isolated mass was recrystalliZed from abs. ethanol.

Yield of 2-(3-thienyl)-1-nitro ethylene 50%, m.p. 94.5 C. 2 g of the above mentioned nitro-ethylene was reduced with LiAlH4 (1.71 g) in dry THF (70 ml) reaction time 2.5 h. Work up with NaOH and subsequent extraction with methylene chloride followed by drying of the organic phase with MgSO4 and evaporation giving 75% of 2-(3-Thienyl) ethanamine which was used without further purification.

7-(4-Chloro-phenyl)-4,5,6,7-tetrahydrothieno[2,3-c]pyridine 2-(3-Thienyl)ethanamine (3.15 g) and 4-chlorobenzaldehyde (3.5 g) were mixed without solvent resulting in dissolution af the crystals of the amine followed by precipitation of slightly yellow crystals. The mixture was left at RT for 4 h. Trifluoroacetic acid (20 ml) was added and the mixture stirred overnight at RT.

The solvent was evaporated and the resulting mixture extracted between NaOH (4M) and methylene chloride, the organic phase was separated, dried with MgSO4/C and evaporated resulting in an oil which was purified on silica gel using methylene chloride/methanol (9/1) as eluent. Yield of 7-(4-Chloro-phenyl)-4,5,6,7-tetrahydrothieno[2,3-cl]yridine 50%, m.p. 93.6–93.8 C.

[7-(4-Chloro-phenyl)-4,5,6,7-tetrahydrothieno[2,3-c]pyridin-6-yl]-(4-methoxy-phenyl)-methanone 7-(4-Chloro-phenyl)-4,5,6,7-tetrahydrothieno[2,3-c]pyridin (100 mg) in toluene (20 ml), 4-methoxybenzoyl chloride (68.3 mg) and triethylamine (1 ml) were mixed and the mixture stirred at RT for 2 h. The reaction mixture was extracted once with NaOH (1 M) and once with water, the organic phase dried (MgSO4) and evaporated to dryness resulting in yellow oil which was purified on silica gel using methylene chloride/methanol 19/1 as eluent. The resulting oil was treated with abs ethanol resulting in precipitation of crystals. Yield 91%, m.p. 129.5–130.0 C. MS. M+=383.

Example 3
[7-(4-Methoxyphenyl)-4,5,6,7-tetrahydrothieno[2,3-c]pyridin-6-yl]-(4-methoxy-phenyl)-methanone

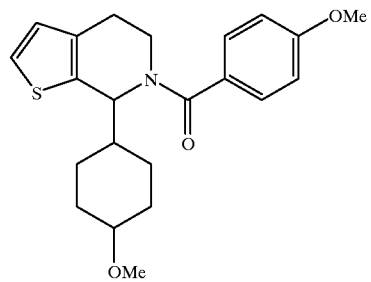

was prepared using the same methods as described in example 2 using 2-(3-thienyl)ethanamine (1.21 g ) and 4-methoxybenzaldehyde (1.30 g ) for the preparation of the imine intermediate (yield 2.4 g) and performing the ring closure with TFA (15 ml).

Yield 42% of 7-(4-methoxyphenyl)-4,5,6,7-tetrahydrothieno[2,3-c]pyridine isolated as an oil. MS: M+=245.
Method a.
[7-(4Methoxyphenyl)-4,5,6,7-tetrahydrothieno[2,3-c]pyridin-6-yl]-(4-methoxy-phenyl)-methanone was prepared from 7-(4-methoxyphenyl)-4,5,6,7-tetrahydrothieno[2,3-c]pyridin (80 mg) in toluene (10 ml), 4-methoxybenzoyl chloride (66.5 mg) and triethylamine (90 uL) as described in example 2. Yield 80% of the title compound, MS: M+=379.
Method b.
[7-(4Methoxyphenyl)-4,5,6,7-tetrahydrothieno[2,3-c]pyridin-6-yi]-(4-methoxy-phenyl)-methanone 7-(4-methoxyphenyl)-4,5,6,7-tetrahydrothieno[2,3-c]pyridine (80 mg) in toluene (10 ml), 4-methoxybenzoic acid (55 mg), EDAC (94 mg) and HOBt (44 mg) were mixed in DMF (3 ml). The mixture was stirred overnight, evaporated to dryness and dissolved in ethyl acetate (10 ml).

The organic phase was successively extracted with 10 ml of each of the following: NaOH (1M), water, HCl (0.1 M), NaOH (1 M), and water, the organic layer dried (MgSO4) and evaporated to dryness giving 100 mg of the title compound (81%), MS: M+=379.

Example 4
[7-(4-Methoxycyclohexyl)-4,5,6,7-tetrahydrothieno[2,3-c]pyridin-6-yl]-(4-methoxyphenyl)-methanone

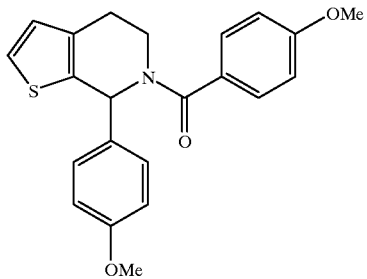

2-(3-Thienyl)ethanamine (3 g) was treated with 4-methoxycyclohexanecarboxylic acid (cis/trans mixture, 3.73 g), HOBT (3.18 g) and EDAC (6.78 g) in DMF (180 ml). The mixture is stirred overnight, evaporated to dryness. The resulting oil was redissolved in methylene chloride (100 ml) and extracted with NaOH (2 M, 100 ml). The organic phase was separated and further extracted consecutively with sat. saline (100 ml), HCl (0.1 M, 100 ml), NaOH (0.5 M, 100 ml).

The organic layer was isolated, dried over MgSO4, yield 5.75g of 4-methoxycyclohexanecarboxylic acid (2-thiophen-3-yl-ethyl)-amide as an oil 93%). The 13C NMR spectrum clearly shows the presence of two isomers (cis and trans). 4-Methoxycyclohexanecarboxylic acid (2-thiophen-3-yl-ethyl)-amide (3.1 g) was dissolved in toluene (50 ml), POCl3 (3.16 ml) dissolved in toluene (100 ml) was added dropwise, and the mixture was heated to 80° C. for 4 h, further stirring overnight at RT.

Subsequently the mixture was cooled to 5° C. NaOH (4 M, 150 ml was added and the organic phase was isolated and washed twice with water, dried (MgSO4) and evaporated to dryness.

Yield 97% of 7-(4-methoxycyclohexyl)-4,5-dihydro-thieno[2,3-c]pyridine, isolated as an oil.

7-(4-Methoxycyclohexyl)-4,5-dihydro-thieno[2,3-c]pyridine (2.45 g) was reduced with NaBH4 (1.11 g) in methanol (50 ml). The mixture was stirred at RT for 2 h and subsequently evaporated and extracted between dichloromethane (100 ml) and water (100 ml). The organic phase was evaporated and the resulting oil was purified on silica gel using dichloromethane /methanol (9/1) as eluent.

Yield 60% of 7-(4-methoxycyclohexyl)-4,5,6,7-tetrahydro-thieno[2,3-c]pyridine. The structure was confirmed by NMR and MS: M+251.

7-(4-Methoxycyclohexyl)-4,5,6,7-tetrahydro-thieno[2,3-c]pyridine (0.1 g), 4-methoxybenzoyl chloride (0.081 g), and triethylamine (0.105 ml) were reacted in toluene (5 ml) as described in example 2.

Reaction time overnight. Rinse up procedure exactly as described in example 2. Yield 0.143 g crude [7-(4-Methoxycyclohexyl)-4,5,6,7-tetrahydrothieno[2,3-c]pyridin-6-yl]-(4-methoxyphenyl)-methanone, MS: M+=385.

Example 5
[7-(1-Methylpiperidin-4-yl)-4,5,6,7-tetrahydrothieno[2,3-c]pyridin-6-yl]-(4-methoxyphenyl)-methanone

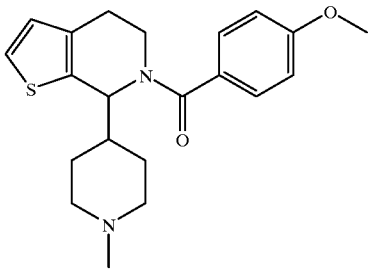

2-(3-Thienyl)ethanamine (3 g) was treated with 1-methylpiperidine-4-carboxylic acid (4.24 g), HOBT (3.18 g), and EDAC (6.78 g) in DMF (180 ml). Procedure exactly as described in example 4. Yield 1.22 g crystals of 1-methylpiperidine-4-carboxylic acid (2-thiophen-3-yl-ethyl)-amide, identified by NMR and MS: M+252.

1-Methylpiperidine-4-carboxylic acid (2-thiophen-3-yl-ethyl)-amide (1.2 g) POCl3 (1.22 ml) were reacted in toluene (50 ml) exactly as described in example 4. 1.1 g of [7-(1-Methylpiperidin-4-yl)-4,5,-dihydrothieno[2,3-c]pyridine was isolated identified by NMR and MS: M+=234.

7-(1-Methylpiperidin-4-yl)-4,5,-dihydrothieno[2,3-c]pyridine (0.1 g), 4-methoxybenzoyl chloride (0.086 g), and triethylamine (0.112 ml) were reacted in toluene (5 ml) exactly as described in example 4. Yield 90% of crude [7-(1-Methylpiperidin-4-yl)-4,5,6,7-tetrahydrothieno[2,3-c]pyridin-6-yl]-(4-methoxyphenyl)-methanone. MS: M+=370.

Example 6
[7-(4-Tetrahydrofuran-3yl)-4,5,6,7-tetrahydrothieno[2,3-c]pyridin-6-yl]-(4-methoxyphenyl)-methanone

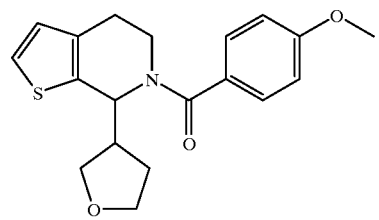

2-(3-Thienyl)ethanamine (3 g) was treated with tetrahydro-3-furoic acid (2.74 g), HOBT (3.18 g), and EDAC (6.78 g) in DMF (180 ml). Procedure exactly as described in example 4. Yield 3.37 g hard oil of tetrahydro-3-furoic acid (2-thiophen-3-yl-ethyl)-amide, identified by NMR and MS M+225.

Tetrahydro-3-furoic acid (2-thiophen-3-yl-ethyl)-amide (3.35 g), POCl3 (4.06 ml) were reacted in toluene (150 ml) exactly as described in example 4. 2.77 g of 4-tetrahydrofuran-3-yl-4,5,-dihydrothieno[2,3-c]pyridine was isolated identified by NMR and MS: M+=207.

7-(4-Tetrahydrofuran-3-yl)-4,5,-dihydrothieno[2,3-c]pyridine (0.1 g), 4-methoxybenzoyl chloride (0.097 9), and triethylamine (0.126 ml) were reacted in toluene (5 ml) exactly as described in example 4. Yield 0.148 g of crude [4-tetrahydrofuran-3-yl-4,5,-dihydrothieno[2,3-c]pyridine]-(4-methoxyphenyl)-methanone. MS: M+=343

Example 7–41

The following compounds were made according to the reaction scheme described in method c) above, using the following reaction conditions:

The carboxylic acid (0.15 mmol), HOBt (0.15 mmol), EDAC (0.15 mmol) and 7-substituted 4,5,6,7-tetrahydrothieno[2,3-c]pyridine (0.15 mmol) were mixed in DMF (1 ml) and stirred at RT overnight.

Ethyl acetate (1.5 ml) and saturated saline (1 ml) were added, the organic phase was separated and evaporated to dryness.

The identity of the product was confirmed by HPLC/MS.

| Example | Structure | HPLC/MS Rt (min) | m/z (M + 1) |
|---|---|---|---|
| 7 | 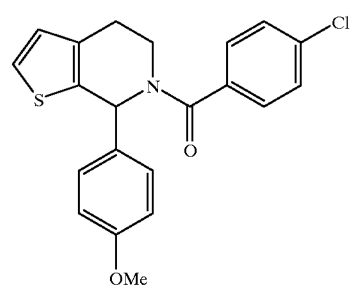 | 15.55 | 384 |

-continued

| Example | Structure | HPLC/MS Rt (min) | m/z (M + 1) |
|---------|-----------|------------------|-------------|
| 8 | 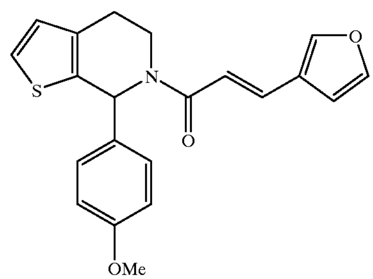 | 14.17 | 366 |
| 9 | 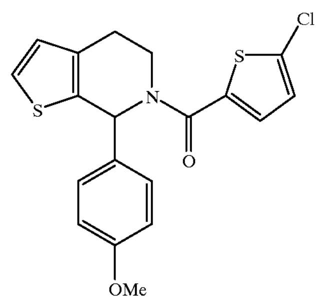 | 16.02 | 390 |
| 10 | 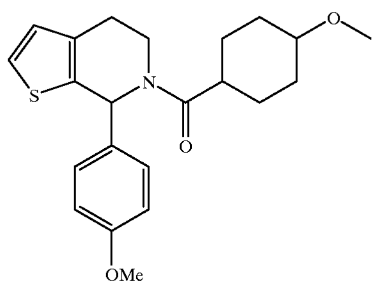 | 13.80 (60%) 13.35 (40%) | 386 |
| 11 | 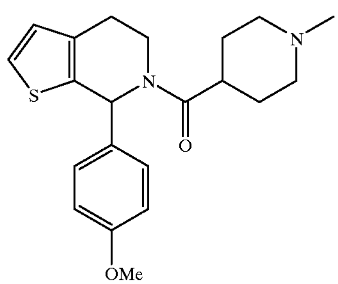 | 8.48 | 371 |
| 12 | 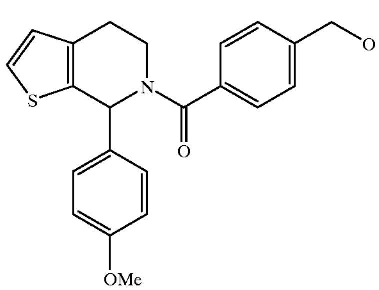 | 11.90 | 380 |

-continued

| Example | Structure | HPLC/MS Rt (min) | m/z (M + 1) |
|---|---|---|---|
| 13 | 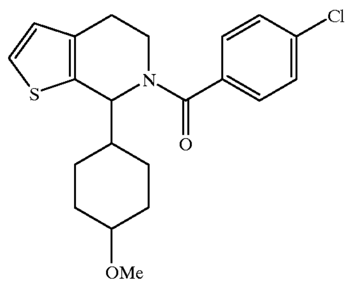 | 14.70 (60%)<br>15.25 (38%) | 390 |
| 14 | 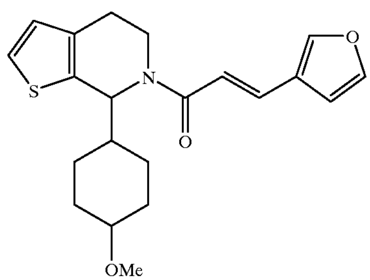 | 13.17 (46%)<br>13.82 (45%) | 372 |
| 15 | 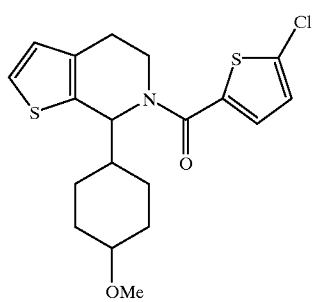 | 15.32 (61%)<br>15.77 (39%) | 396 |
| 16 | 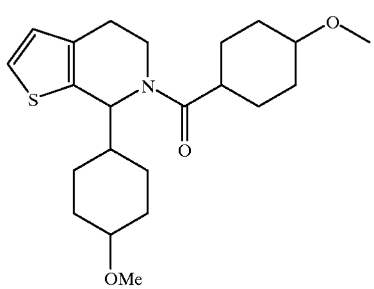 | 12.89 (26%)<br>12.87 (25%)<br>12.28 (22%)<br>13.58 (20%) | 392 |
| 17 | 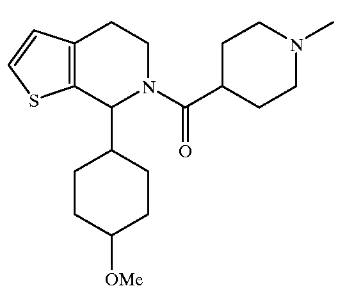 | 8.20 (14.5%)<br>8.53 (11%) | 377 |

-continued
| Example | Structure | HPLC/MS Rt (min) | m/z (M + 1) |
|---|---|---|---|
| 18 | 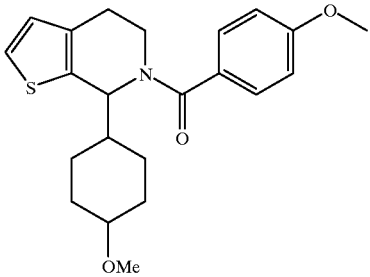 | 10.73 (62%) 11.57 (34%) | 386 |
| 19 | 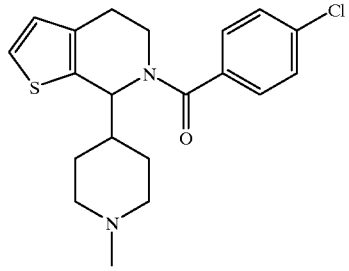 | 8.73 | 375 |
| 20 | 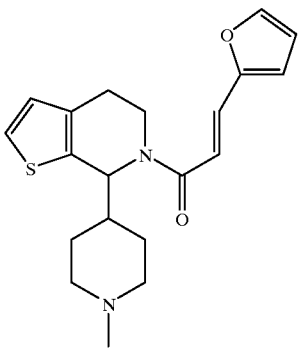 | 8.23 | 357 |
| 21 | 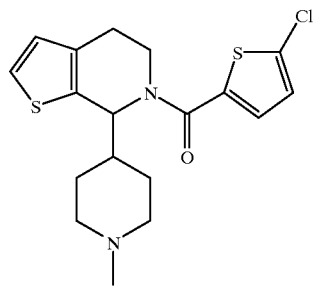 | 8.67 | 381 |
| 22 | 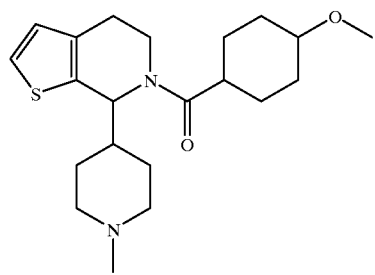 | 7.95 (61%) 7.60 (38%) | 377 |

-continued
| Example | Structure | HPLC/MS Rt (min) | m/z (M + 1) |
|---|---|---|---|
| 23 | 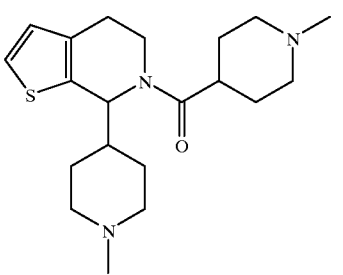 | 5.68 | 362 |
| 24 | 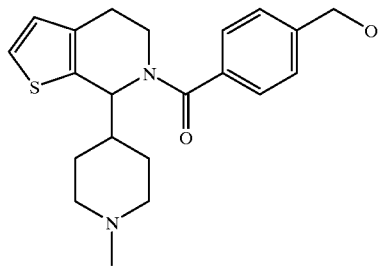 | 7.14 | 371 |
| 25 | 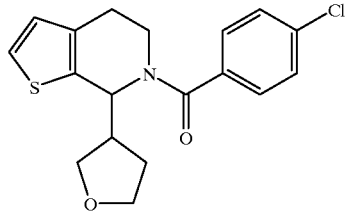 | 13.12 | 348 |
| 26 | 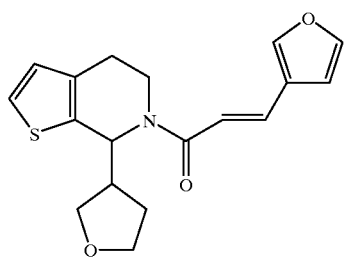 | 11.57 | 330 |
| 27 | 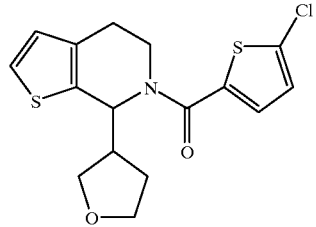 | 13.63 | 354 |

-continued

| Example | Structure | HPLC/MS Rt (min) | m/z (M + 1) |
|---|---|---|---|
| 28 | 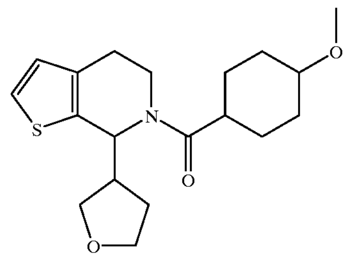 | 10.12 (54%) 10.62 (31%) | 350 |
| 29 | 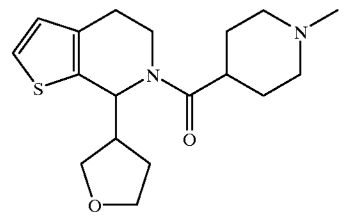 | 6.92 | 335 |
| 30 | 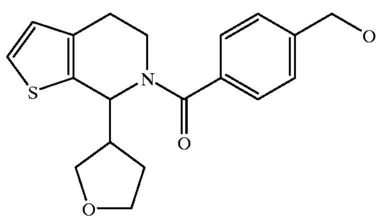 | 9.17 (58%) 9.35 (37%) | 344 |
| 31 | 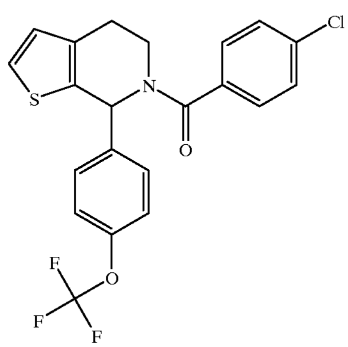 | 17.22 | 438 |
| 32 | 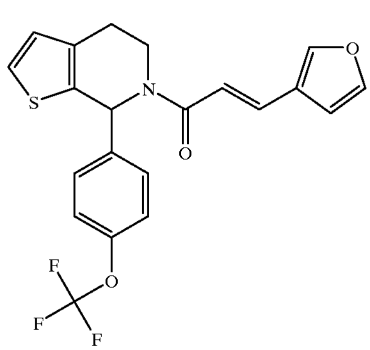 | 16.05 | 420 |

-continued

| Example | Structure | HPLC/MS Rt (min) | m/z (M + 1) |
|---|---|---|---|
| 33 | 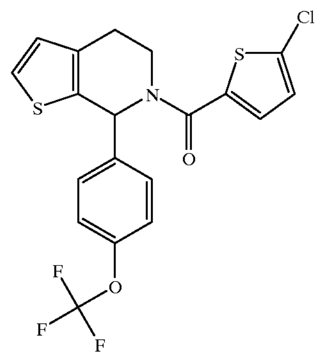 | 17.63 | 444 |
| 34 | 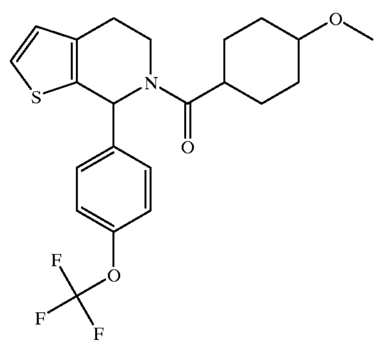 | 16.02 (60%)<br>15.73 (39%) | 440 |
| 35 | 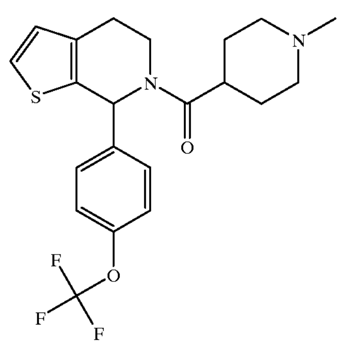 | 9.88 | 425 |
| 36 | 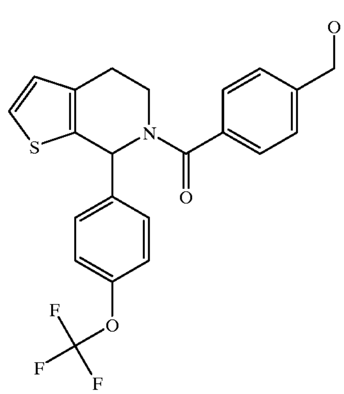 | 14.38 | 434 |

-continued

| Example | Structure | HPLC/MS Rt (min) | m/z (M + 1) |
|---|---|---|---|
| 37 | 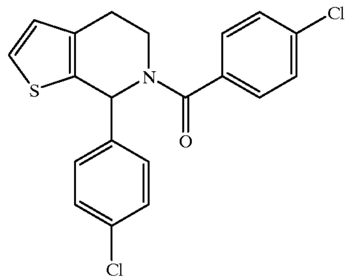 | 16.75 | 389 |
| 38 | 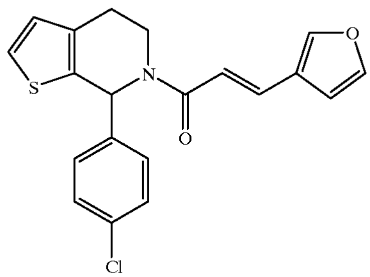 | 15.48 | 370 |
| 39 | 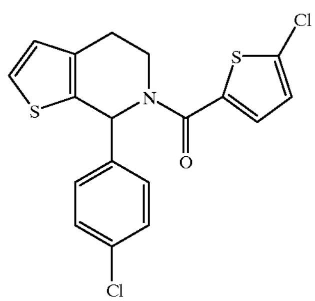 | 17.25 | 395 |
| 40 | 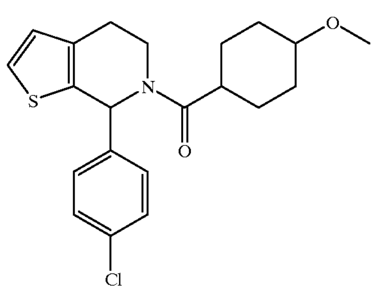 | 15.40 (60%)<br>15.08 (37%) | 390 |
| 41 | 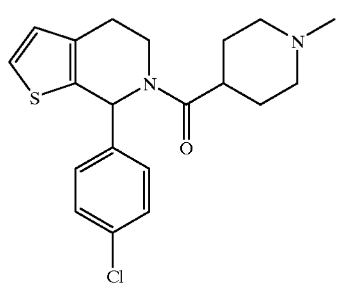 | 9.43 | 376 |

Example 42–65

The following compounds were made according to the reaction scheme described in method (c) above using the following reaction conditions:

7-substituted 4,5.6,7-tetrahydrothieno[2,3-c] pyridine (125 mg, 1 eqv), the carboxylic acid (1.1 eqv), HOBt (1.5eqv) and EDAC (1.0 eqv) were mixed in DMF (1 ml) and stirred at RT overnight.

Dichloromethane (4 ml) was added and the mixture extracted with the following series of solvents: a) NaOH (1M, 4 ml); b) H2O (4 ml); c) HCl (1M, 4 ml); d) H2O (4 ml) and e) brine (4 ml).

The resulting organic phase was separated and evaporated to dryness.

The identity of the product was confirmed by HPLC/MS.

| Example | STRUCTURE | HPLC/MS, m/z (M + 1) |
|---|---|---|
| 42 | 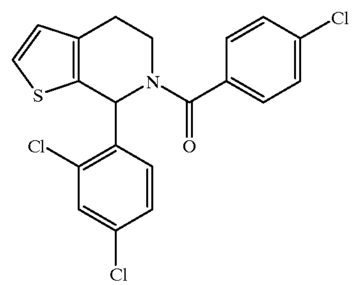 | m/z: 421 RT: 7.12 ELS: 65% |
| 43 | 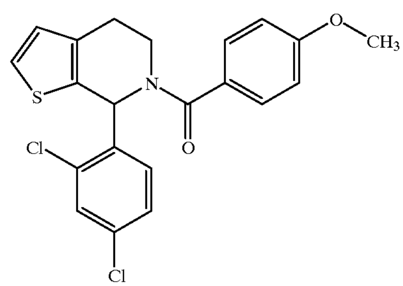 | m/z: 417 RT: 6.71 ELS: 50% |
| 44 | 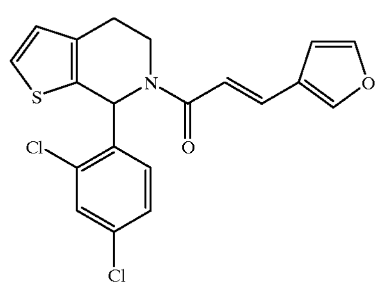 | m/z: 404 RT: 6.58 ELS: 98% |
| 45 | 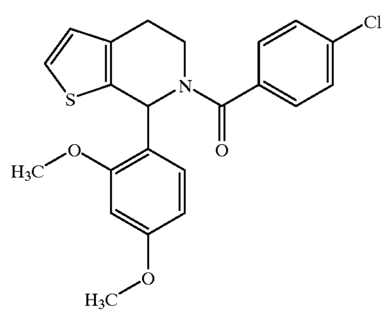 | m/z: 413 RT: 6.29 ELS: 70% |

-continued
| Example | STRUCTURE | HPLC/MS, m/z (M + 1) |
|---|---|---|
| 46 | 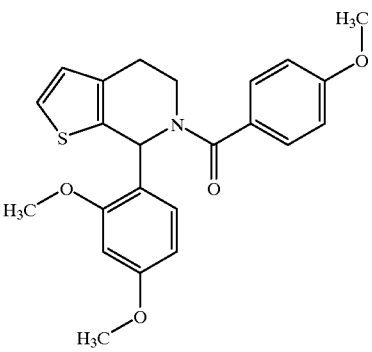 | m/z: 409 RT: 5.82 ELS: 77% |
| 47 | 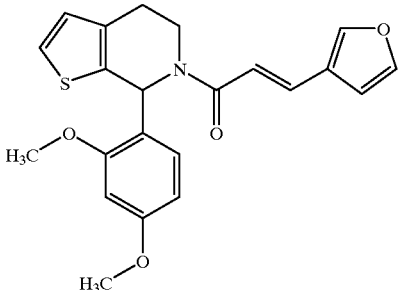 | m/z: 395 RT: 5.78 ELS: 98% |
| 48 | 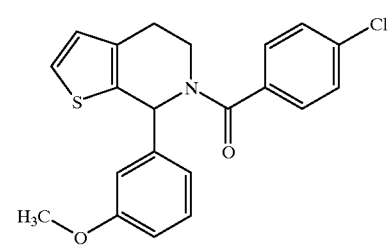 | m/z: 384 RT: 6.39 ELS: 100% |
| 49 | 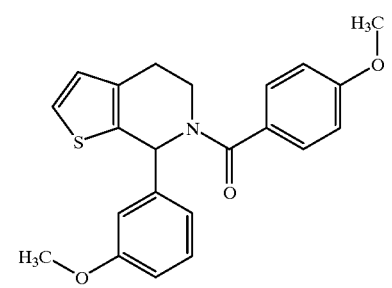 | m/z: 380 RT: 5.39 ELS: 73% |
| 50 | 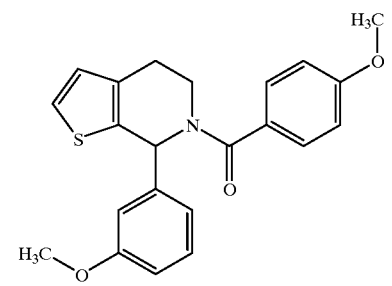 | m/z: 365 RT: 5.85 ELS: 100% |

-continued
| Example | STRUCTURE | HPLC/MS, m/z (M + 1) |
|---|---|---|
| 51 | 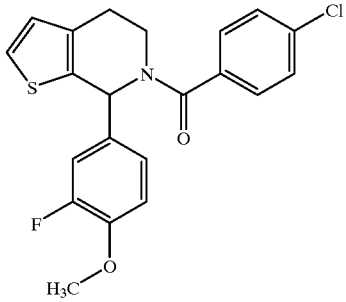 | m/z: 401 RT: 6.40 ELS: 401 |
| 52 | 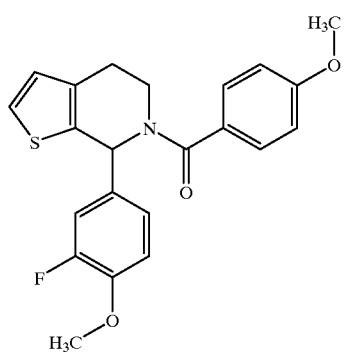 | m/z: 397 RT: 5.97 ELS: 64% |
| 53 | 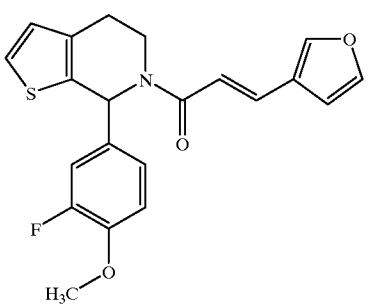 | m/z: 383 RT: 5.87 ELS: 100% |
| 54 | 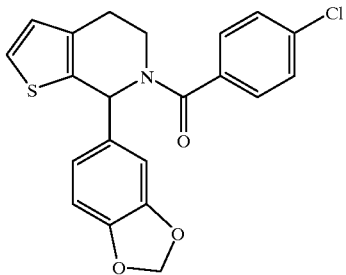 | m/z: 397 RT: 6.30 ELS: 97% |
| 55 | 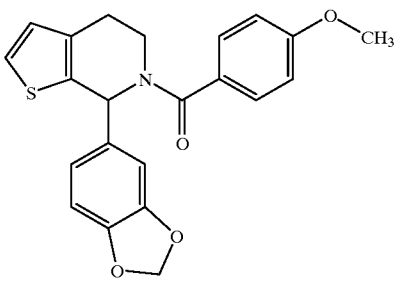 | m/z: 394 RT: 5.87 ELS: 73% |

-continued

| Example | STRUCTURE | HPLC/MS, m/z (M + 1) |
|---------|-----------|----------------------|
| 56 | 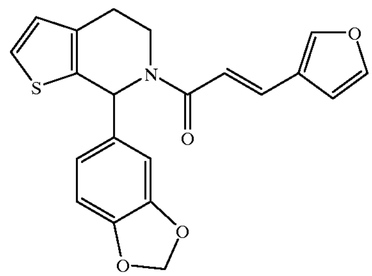 | m/z: 379 RT: 5.77 ELS: 100% |
| 57 | 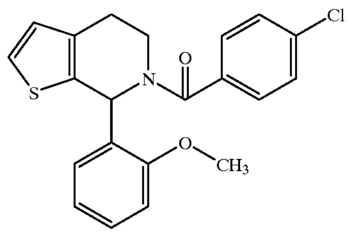 | m/z: 384 RT: 6.37 ELS: 100% |
| 58 | 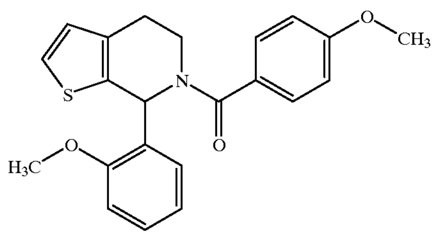 | m/z: 380 RT: 5.38 ELS: 75% |
| 59 | 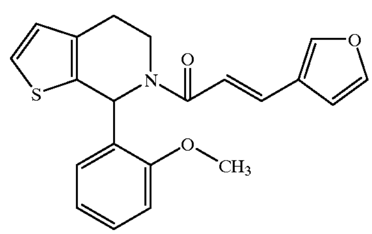 | m/z: 366 RT: 5.84 ELS: 100% |
| 60 | 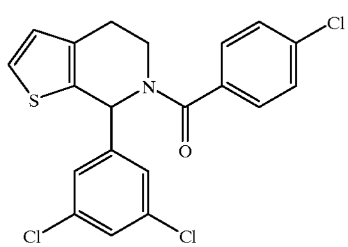 | m/z: 422 RT: 7.36 ELS: 95% |
| 61 | 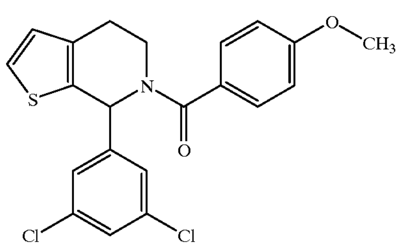 | m/z: 418 RT: 6.97 ELS: 80% |

-continued

| Example | STRUCTURE | HPLC/MS, m/z (M + 1) |
|---|---|---|
| 62 | 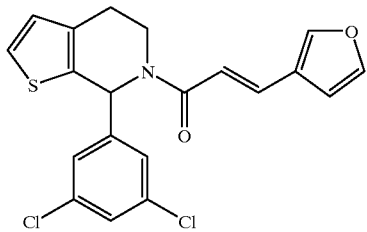 | m/z: 404 RT: 6.88 ELS: 100% |
| 63 | 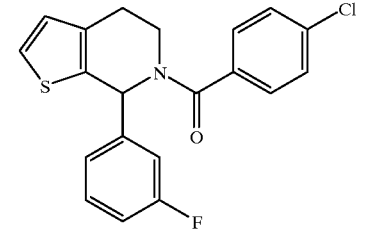 | m/z: 372 RT: 6.52 ELS: 100% |
| 64 | 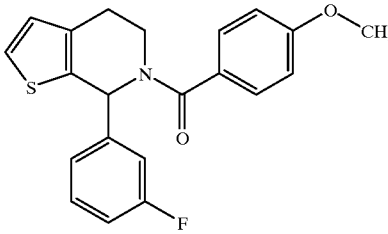 | m/z: 368 RT: 5.38 ELS: 67% |
| 65 | 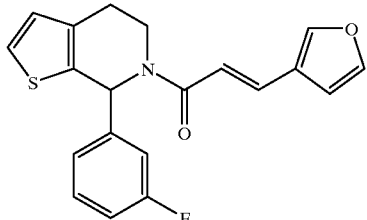 | m/z: 354 RT: 6.00 ELS: 100% |

Example 66.

7-substituted 4,5,6,7-tetrahydrothieno[2,3-c]pyridine intermediates.

The 7-substituted 4,5,6,7-tetrahydrothieno[2,3-c]pyridine intermediates were prepared as described in example 2 from equimolar amounts of appropriate substituted benzaldehyde (0.0078 mol) and 2-(3-thienyl)ethaneamine (0.0078 mol) in dry ethanol (8 ml) by shaking for 3 days at room temperature. The mixture was subsequently evaporated to dryness and the resulting oil treated with trifluoroacetic acid (20 ml) by stirring for 24h followed by addition af NaOH (2M, 10 ml). Extraction with dichloromethane (10 ml) followed by evaporation gave the required starting 7-substituted 4,5,6,7-tetrahydrothieno[2,3-c]pyridines.

Identity and yield estimated from the HPLC/MS spectra.

| STRUCTURE | LC-MS (electrospray) |
|---|---|
| 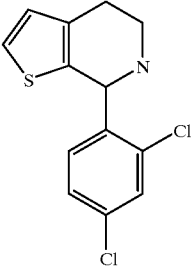 | m/z: 284 RT: 4.47 ELS: 91% |
| 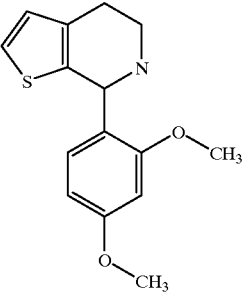 | m/z: 276 RT: 4.20 ELS: 95% |
| 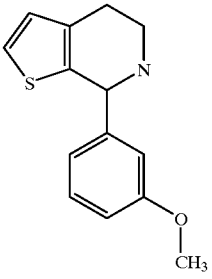 | m/z: 246 RT: 4.12 ELS: 100% |
| 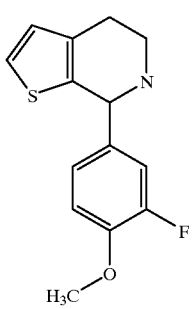 | m/z: 264 RT: 4.17 ELS: 97% |
| 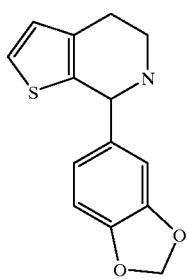 | m/z: 260 RT: 4.05 ELS: 100% |

| STRUCTURE | LC-MS (electrospray) |
|---|---|
| 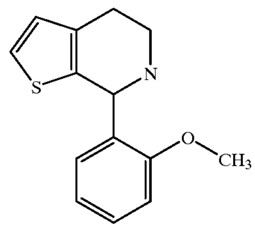 | m/z: 246 RT: 4.15 ELS: 100% |
| 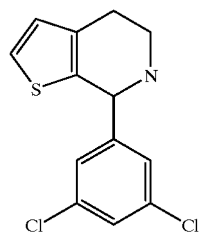 | m/z: 284 RT: 4.62 ELS: 94% |
| 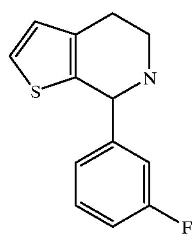 | m/z: 233 RT: 4.08 ELS: 100% |
| 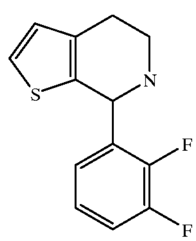 | m/z: 252 RT: 3.97 ELS: 90% |

General:

The HPLC-MS analyses were performed on a PE Sciex API 100 LC/MS System using a Waters™ 3 mm×150 mm 3.5 μC-18 Symmetry column and positive ionspray with a flow rate at 20 μL/minute. The column was eluted with a linear gradient of 5–90% A, 85–0% B and 10% C in 15 minutes at a flow rate of 1 ml/min (solvent A=acetonitrile, solvent B=water and solvent C=0.1% trifluoroacetic acid in water).

What is claimed is:

1. A compound of formula I

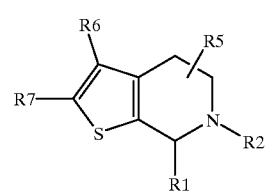

Formula (I)

wherein

R1 is an unsaturated straight or branched $C_{2-8}$-hydrocarbon chain optionally substituted with one or more substituents,
 a saturated $C_{3-8}$-alicyclic hydrocarbon group optionally substituted with one or more substituents,
 an unsaturated $C_{5-8}$-alicyclic hydrocarbon group optionally substituted with one or more substituents,
 Q optionally substituted with one or more substituents or
 aryl optionally substituted with one or more substituents;

R2 is a saturated $C_{3-8}$-alicyclic hydrocarbon group optionally substituted with one or more substituents,
 an unsaturated $C_{5-8}$-alicyclic hydrocarbon group optionally substituted with one or more substituents,
 aralkyl optionally substituted with one or more substituents or
 COR3 optionally substituted with one or more substituents;
 with the proviso that when R1 is aryl optionally substituted with one or more substituents R2 may not be aralkyl optionally substituted with one or more substituents;

R3 is a saturated straight or branched $C_{1-8}$-hydrocarbon chain optionally substituted with one or more substituents,
  an unsaturated straight or branched $C_{2-8}$-hydrocarbon chain optionally substituted with one or more substituents,
  a saturated $C_{3-8}$-alicyclic hydrocarbon group optionally substituted with one or more substituents,
  an unsaturated $C_{5-8}$-alicyclic hydrocarbon group optionally substituted with one or more substituents,
  an aryl optionally substituted with one or more substituents,
  an aralkyl optionally substituted with one or more substituents or
  W optionally substituted with one or more substituents;
Q and W are independently selected from the group consisting of

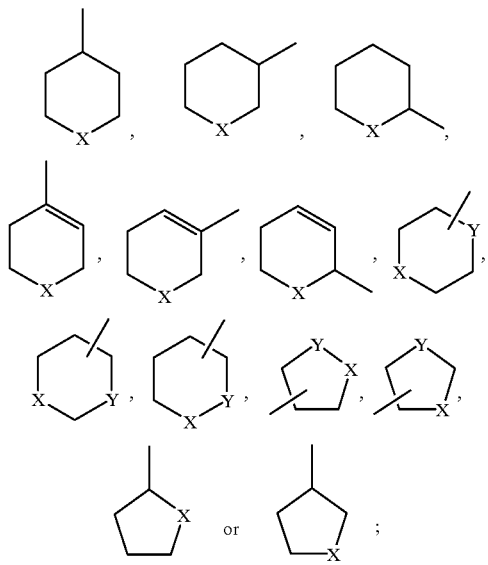

X and Y are independently selected from the group consisting of NR4, O, S, >SO and >SO$_2$;
  and R4 is selected from the group consisting of hydrogen,
    a saturated straight or branched $C_{1-8}$-hydrocarbon chain optionally substituted with one or more substituents,
    an unsaturated straight or branched $C_{2-8}$-hydrocarbon chain optionally substituted with one or more substituents,
    a saturated $C_{3-8}$-alicyclic hydrocarbon group optionally substituted with one or more substituents,
    an unsaturated $C_{5-8}$-alicyclic hydrocarbon group optionally substituted with one or more substituents,
    $C_{1-8}$-acyl, $C_{1-8}$-alkoxycarbonyl, or mono- or dialkyl-carbamoyl;
R5, R6 and R7 are independently selected from amino-$C_{1-6}$-alkyl, hydroxy-$C_{1-6}$-alkyl, hydrogen, $C_{1-6}$-alkyl, aryl, aralkyl, aryloxy, aryloxy-$C_{1-6}$-alkyl, benzyl, halogen, hydroxy, mercapto, cyano, nitro, carboxy, carbamoyl, CONHC$_{1-4}$-alkyl, CON(C$_{1-4}$alkyl)$_2$, $C_{1-4}$-acyl, $C_{1-4}$-alkoxy, $C_{1-4}$-alkylthio, —SOC$_{1-6}$-alkyl, —SO$_2$C$_{1-6}$-alkyl, $C_{1-4}$-alkoxycarbonyl, $C_{1-4}$-alkanoyloxy, amino, optionally substituted mono- or di-$C_{1-6}$-alkylamino, acylamino, —NC$_{1-4}$-alkylCOC$_{1-4}$-alkyl, —SO3H, —SO2NH-$C_{1-6}$-alkyl, tetrazolyl, perhalomethyl, and perhalomethoxy,
  each of the above substituents being selected from the group consisting of halogen, hydroxyl, carboxy, carboxyalkenyl, 2-carboxyethenyl, cyano, nitro, carbamoyl, $C_{1-8}$-alkylcarbamoyl, $C_{1-8}$-acyl, acetamido, $C_{1-8}$-alkoxy, $C_{1-8}$-alkyl, $C_{1-8}$-alkoxycarbonyl, $C_{1-8}$-alkanoyloxy, $C_{1-4}$-alkylthio, $C_{1-4}$-alkylsulphinyl, $C_{1-4}$-alkylsulphonyl, $C_{1-8}$-alkylamino, $C_{1-8}$-dialkylamino, $C_{2-6}$-cycloamines, aminoalkyl, aminoalkoxy, aryl, aryloxy, aralkyloxy, hydroxyalkyl, perhaloalkoxy, alkoxyaryl, perhaloalkyl, oxo, $C_{1-4}$-alkanoylamino-$C_{1-4}$-alkyl, alkoxyoxoindanyl, dimethylhydrazidyl, methylendioxy, thioxothiazolyl, imidazolyl and 2-morpholin-4-ylethoxy;
  or a salt thereof with a pharmaceutically acceptable acid or base, or any optical isomer or mixture of optical isomers or any tautomeric form.

2. A compound of claim 1, wherein R5, R6 and R7 are hydrogen.

3. A compound of claim 1, wherein R2 is COR3.

4. A compound of claim 1 wherein R1 is Q optionally substituted with one or more substituents and Q is

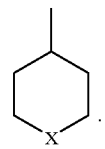

5. A compound of claim 4 wherein X is NR4 or O.

6. A compound of claim 1 wherein R1 is Q optionally substituted with one or more substituents and Q is

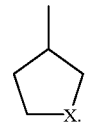

7. A compound of claim 6 wherein X is O.

8. A compound of claim 1 wherein R3 is a saturated straight or branched $C_{1-8}$-hydrocarbon chain optionally substituted with one or more substituents.

9. A compound of claim 1 wherein R3 is an unsaturated straight or branched $C_{2-8}$-hydrocarbon chain optionally substituted with one or more substituents.

10. A compound of claim 1 wherein R3 is a saturated $C_{3-8}$-alicyclic hydrocarbon group optionally substituted with one or more substituents.

11. A compound of claim 1 wherein R3 is an aryl optionally substituted with one or more substituents.

12. A compound of claim 1 wherein R3 is W optionally substituted with one or more substituents.

13. A compound of claim 12 wherein W is

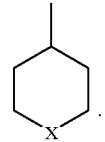

14. A compound of claim 13 wherein X is NR4.

15. A pharmaceutical composition comprising, as an active ingredient, a therapeutically effective amount of a compound of claim 1, together with a pharmaceutically acceptable carrier or diluent.

16. The pharmaceutical composition of claim 15 in the form of an oral dosage unit or a parenteral dosage unit.

17. A compound of claim 1 characterized by having a glucose-6-phosphatase inhibitory activity corresponding to an $IC_{50}$ value of less than 100 μM.

18. A method of treating or preventing diseases of the endocrinologic system comprising administering to a subject in need thereof a therapeutically effective amount of a compound of claim 1.

19. A method of treating or preventing hyperglycemia or diabetes in a subject in need thereof comprising administering to the subject a therapeutically effective amount of a compound of claim 1.

20. A compound of claim 1 wherein R1 is N-methylpiperidinyl, tetrahydrofuryl or tetrahydropyranyl.

21. A compound of claim 1 wherein R1 is optionally substituted phenyl, thienyl, furanyl, Benzo[1,3]dioxol, pyridyl or cyclohexyl.

22. A compound of claim 21 wherein the substituents of R1 are selected from the group consisting of halogen, perhaloalkyl, perhaloalkoxy, $C_{1-6}$-alkoxy, $C_{1-8}$-alkyl, $C_{1-8}$-alkylamino, $C_{1-8}$-dialkylamino and $C_{2-5}$-cycloalkylamino.

23. A compound of claim 1 wherein R1 is selected from the group consisting of phenyl, 4-chlorophenyl, 3-fluorophenyl, 2,4-chlorophenyl, 3,5-chlorophenyl, 2-methoxyphenyl, 3-methoxyphenyl, 4-methoxyphenyl, 2,4-methoxyphenyl, 3-fluoro-4-methoxyphenyl, 4-trifluoromethylphenyl, 4-trifluoromethoxyphenyl, 4-dimethylaminophenyl, 4-pyridyl, 2-thienyl, 5-chloro-2-thienyl, 3-chloro-2-thienyl, Benzo[1,3]dioxol-5yl, cyclohexyl and 4-methoxycyclohexyl.

24. A compound of claim 1 wherein R3 is cyclohexyl, phenyl, alkoxyphenyl, dialkoxyphenyl, hydroxyphenyl, indanyl, imidazolyl, pyridyl, benzofuranyl, indolyl, benzimidazolyl, thienyl, furanyl, or pyranyl, each of which is optionally substituted with one or more substituents.

25. A compound of claim 14 wherein R4 is methyl or methanoyl.

26. A compound of claim 1 wherein R2 is COR3 and R3 is selected from the group consisting of phenyl, 3-methoxyphenyl, 4-methoxyphenyl 4-chlorophenyl, 4-trifluoromethylphenyl, 4-methylphenyl, 3,4-dimethoxyphenyl, 4-ethoxyphenyl, 4-fluorophenyl, 4-trifluoromethoxyphenyl, 4-dimethylaminophenyl, 4-bromophenyl, 4-hydroxyphenyl, 4-hydroxymethylphenyl, 4-nitrophenyl, 4-cyanophenyl, 4-methylthiophenyl, 4-methylsulfonylphenyl, 4-acetylphenyl, 4-acetamidophenyl, 4-acetoxyphenyl, 3,4-methylenedioxyphenyl, 3,4-dimethoxyphenyl, 3-chloro-4-methoxyphenyl, indolyl, 1H-indol-5-yl, and 1H-benzimidazol-5-yl, 2-(4-methoxyphenyl)-ethenyl, 2-(3-methoxyphenyl)-ethenyl, 2-(4-chlorophenyl)-ethenyl, 2-(4-fluorophenyl)-ethenyl, 2-(4-trifluoromethylphenyl)-ethenyl, 2-(4-methoxyphenyl)-ethyl, 2-(4-chlorophenyl)-ethyl, 4-chlorobenzyl, 4-methoxybenzyl, 2-(2-furyl)-ethenyl, 2-(4,5-dimethyl-2-furyl)-ethenyl, 2-(5-methyl-2-furyl)-ethenyl, 2-(3-furyl)-ethenyl, 2-(2-thienyl)-ethenyl, 2-(3-thienyl)-ethenyl, 4-methoxyphenyl-2-ethenyl, 4-pyridyl, 5-hydroxypyrazin-2-yl, 5-chloro-6-hydroxypyridin-3-yl, 2-chloropyridin-3-yl, benzofuran-2-yl, benzothiophen-2-yl-, 7-methoxybenzofuran-2-yl, furyl, thienyl, chlorothienyl, 5-chlorothiophen-2-yl, benzimidazol, 1 H-benzimidazol-5-yl, 4-methoxycyclohexyl, 4-oxycyclohexyl, N-methylpiperidinyl, tetrahydrofuryl, tetrahydropyranyl, 4-(2-carboxyethenyl)phenyl, 4-(2-dimethylaminoethoxy) phenyl and 4-(2-morpholin-4-ylethoxy)phenyl.

* * * * *